(12) United States Patent
Takemoto et al.

(10) Patent No.: US 6,576,439 B1
(45) Date of Patent: Jun. 10, 2003

(54) IKK3 KINASE

(75) Inventors: Yoshihiro Takemoto, Tsukuba (JP); Yutaka Sakai, Tsukuba (JP); Yasuhiro Hashimoto, Shinagawa-Ku (JP)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/868,758

(22) PCT Filed: Dec. 24, 1999

(86) PCT No.: PCT/JP99/07286

§ 371 (c)(1),
(2), (4) Date: Jun. 21, 2001

(87) PCT Pub. No.: WO00/39308

PCT Pub. Date: Jul. 6, 2000

(30) Foreign Application Priority Data

Dec. 24, 1998 (GB) .............................................. 9828704

(51) Int. Cl.[7] .............................. C12Q 1/48; C12N 9/12; C12N 15/00; C12N 1/20; C12N 5/00
(52) U.S. Cl. ...................... 435/15; 435/194; 435/320.1; 435/325; 435/252.3; 435/6

(58) Field of Search ................................ 435/15, 6, 194, 435/320.1, 325, 252.3

(56) References Cited

FOREIGN PATENT DOCUMENTS

| WO | WO98/54963 | 12/1998 |
|---|---|---|
| WO | WO00/08179 | 2/2000 |

OTHER PUBLICATIONS

Nagase, T. et al., "Prediction of the Coding Sequences of Unidentified Human Genes. IV. The Coding Sequences of 40 New Genes (KIAA0121–KIAA0160) Deduced by Analysis of CDNA Clones from Human Cell Line KG–1, " DNA Research, vol. 2, No. 4, Aug. 31, 1995, pp. 167–174.

Shimada, T. et al., "IKK–I, a novel lipopolysaccharide–inducible kinase that is related to IkappaB kinases," International Immunology, vol. 11, No. 8, Aug. 1999, pp. 1357–1362.

*Primary Examiner*—M. Monshipouri
(74) *Attorney, Agent, or Firm*—Virginia C. Bennett

(57) ABSTRACT

This invention relates to an IKK kinase protein, IKK3, nucleotides coding for it vectors and host cells containing the same and methods for screening for modulators of said IKK3 protein for treatment of conditions involving inflammation.

3 Claims, 22 Drawing Sheets

FIG. 3a

```
                  .   .  **  *        *        ...         .*.*
**
IKK1
        MERPPGLRPGAGGPWEMRERLGTGGFGNVCLYQHRELDLKIAIKSCRLELSTKNRERWCH
60
IKK2
        MSWSPSLTTQTCGAWEMKERLGTGGFGNVIRWHNQETGEQIAIKQCRQELSPRNRERWCL
60
IKK3            ------
MQSTANYLWHTDDLLGQGATASVYKARNKKSGELVAVKVFNTTSYLRPREVQVR        54

*  .....*.* *.*    * *            .* **** * *    * **. ** *
IKK1
        EIQIMKKLNHANVVKACDVPEELN-ILIHDVPLLAMEYCSGGDLRKLLNKPENCCGLKES
119
IKK2
        EIQIMRRLTHPNVVAARDVPEGMQNLAPNDLPLLAMEYCQGGDLRKYLNQFENCCGLREG
120
IKK3
        EFEVLRKLNHQNIVKLFAVEETGG---S-RQKVLVMEYCSSGSLLSVLESPENAFGLPED
110

*  .*    . . .   *.** *.***.** **.       . * *. * * *...*
IKK1
        QILSLLSDIGSGIRYLHENKIIHRDLKPENIVLQDVG-GKIIHKIIDLGYAKDVDQGSLC
178
IKK2
        AILTLLSDIASALRYLHENRIIHRDLKPENIVLQQGE-QRLIHKIIDLGYAKELDQGSLC
179
IKK3
        EFLVVLRCVVAGMNHLRENGIVHRDIKPGNIMRLVGEEGQSIYKLTDFGAARELDDDEKF
170

*  ** .** *.. *          ... *** ** *   . ..* **.      *
IKK1
        TSFVGTLQYLAPELFE--------NKPYTATVDYWSFGTMVFECIAGYRPFLHHLQP---
227
IKK2
        TSFVGTLQYLAPELLE--------QQKYTVTVDYWSFGTLAFECITGFRPFLPNWQP---
228
IKK3
        VSVYGTEEYLHPDMYERAVLRKPQQKAFGVTVDLWSIGVTLYHAATGSLPFIPFGGPRRN
230

.   .         * . *  **    *    .      * .*
IKK1
        --FTWHEKIKKKDPKCIFACEEMSGEVRFSSHLPQPNSLCSLIVEPMENWLQLMLNWDPQ
285
IKK2
        --VQWHSKVRQKSEVDIVVSEDLNGTVKFSSSLPYPNNLNSVLAERLEKWLQLMLMWHPR
286
IKK3
        KEIMYRITTEKPAGAIAGAQRRENGPLEWSYTLPITCQLSLGLQSQLVPILANILEVEQA
290

*    **. .**.   .            ..   . ..*
IKK1
        QRGGPVDLTLKQPRCFVLMDHILNLKIVHILNMTSAKIISFLLPPDESLHSLQSRIERET
345
IKK2
        QRG-TDPTYGPNGCFKALDDILNLKLVHILNMVTGTIHTYPVTEDESLQSLKARIQQDT
344
IKK3
        KCWG-------FDQFFAETSDILQRVVVHVFSLSQAVLHHIYIHAHNTIAIFQEAVHKQT
343

** * *   ...   ..*  .                         . *
IKK1
        GINTGSQELLSETGISLDPRKPASQCVLDG----VRGCDSYMVYLFDKSKTVYEGPFASR
401
IKK2
        GIPEEDQELLQEAGLALIPDKPATQCISDGKLNEGHTLDMDLVFLFDNSKITYETQISPR
404
IKK3
        SVAPRHQEYLFEGHLCVLEPSVSAQHIAHT------TASSPLTLFS----TAIPKGLAFR
```

```
             *.          .      .    . .*.*  .                   .   ..
IKK1   SYSDSTEMVKIIVHTVQSQDRVLKELFGHLSKLLGCKQKIIDLLPKVEVALSNIKEADNT      638
IKK2   TEGDSQEMVRLLLQAIQSFEKKVRVIYTQLSKTVVCKQKALELLPKVEEVVSLMNEDEKT      642
IKK3   KQFKKSRMRPGLGYNEEQIHKLDKVNFSHLAKRLLQVFQEECVQKYQASLVTHG----KR      610

.  ..  *.     .*  . *.            .            *          .
IKK1   VMFMQGKRQKEIWHLLKIACTQSSARSLVGSSLEGA--VTPQTSAWLPPTSAEHDHSLSC      696
IKK2   VVRLQEKRQKELWNLLKIACSK--VRGPVSGSPD-----SMNASRLSPGQLMSQPSTAS       695
IKK3   MRVVHETRN----HLRLVGCSVAACNTEAQGVQESLSKLLEELSHQLLQDRAKGAQASPP      666

*      ..       .       .         .  *
IKK1   VVTPQDGETSAQMIEENLNCLGHLSTIIHEANEEQGNSMMNLDWSWLTE-----------      745
IKK2   NSLPEPAKKSEELVAEAHNLCTLLENAIQDTVREQDQSFTALDWSWLQTEEEEHSCLEQA      756
IKK3   PIAPYPSPTRKDLLLHMQELCEGMKLLASDLLD-NNRIIERLNRVPAPPDV---------      716

IKK1   -
IKK2   S                                                                757
IKK3   -
```

```
LOCUS       D63485       3221 bp    mRNA          PRI       10-JUL-1997
DEFINITION  Human mRNA for KIAA0151 gene, complete cds.
ACCESSION   D63485
NID         g1469883
KEYWORDS    KIAA0151.
SOURCE      Homo sapiens male myeloblast cell_line:KG-1 cDNA to mRNA.
  ORGANISM  Homo sapiens
            Eukaryotae; mitochondrial eukaryotes; Metazoa; Chordata;
            Vertebrata; Mammalia; Eutheria; Primates; Catarrhini; Hominidae;
            Homo.
REFERENCE   1  (bases 1 to 3221)
  AUTHORS   Nomura,N.
  TITLE     Direct Submission
  JOURNAL   Submitted (13-JUL-1995) to the DDBJ/EMBL/GenBank databases. Nobuo
            Nomura, Kazusa DNA Research Institute, Gene Structure 1; 1532-3
            Yana, Kisarazu, Chiba 292, Japan (E-mail:cdnainfo@kazusa.or.jp,
            Tel:0438-52-3930, Fax:0438-52-3931)
            URL:http://www.kazusa.or.jp,
REFERENCE   2  (bases 1 to 3221)
```

```
AUTHORS    Nomura,N.
JOURNAL    Unpublished (1996)
REFERENCE  3 (sites)
AUTHORS    Nagase,T., Seki,N., Tanaka,A., Ishikawa,K. and Nomura,N.
TITLE      Prediction of the coding sequences of unidentified human genes. IV.
           The coding sequences of 40 new genes (KIAA0121-KIAA0160) deduced by
           analysis of cDNA clones from human cell line KG-1
JOURNAL    DNA Res. 2 (4), 167-174 (1995)
MEDLINE    96127530
FEATURES            Location/Qualifiers
     source          1..3221
                     /organism="Homo sapiens"
                     /db_xref="taxon:9606"
                     /cell_line="KG-1"
                     /cell_type="myeloblast"
                     /sex="male"
     5'UTR           1..326
     gene            327..2477
```

FIG. 4b

CDS 327..2477
/gene="KIAA0151"
/gene="KIAA0151"
/note="The KIAA0151 gene product is classified into serine/threonine kinase."
/citation=[3]
/codon_start=1
/db_xref="PID:d1010418"
/db_xref="PID:g1469884"
/translation="MQSTANYLWHTDDLLGQGATASVYKARNKKSGELVAVKVFNTTS
YLRPREVQVREFEVLRKLNHQNIVKLFAVEETGGSRQKVLVMEYCSSGSLLSVLESPE
NAFGLPEDEFLVVLRCVVAGMNHLRENGIVHRDIKPGNIMRLVGEEGQSIYKLTDFGA
ARELDDDEKFVSVYGTEEYLHPDMYERAVLRKPQQKAFGVTVDLWSIGVTLYHAATGS
LPFIPFGGPRRNKEIMYRITTEKPAGAIAGAQRRENGPLEWSYTLPITCQLSLGLQSQ
LVPILANILEVEQAKCWGFDQFFAETSDILQRVVVHVFSLSQAVLHHIYIHAHNTIAI
FQEAVHKQTSVAPRHQEYLFEGHLCVLEPSVSAQHIAHTTASSPLTLFSTAIPKGLAF
RDPALDVPKFVPKVDLQADYNTAKGVLGAGYQALRLARALLDGQELMFRGLHWVMEVL
QATCRRTLEVARTSLLYLSSSLGTERFSSVAGTPEIQELKAAAELRSRLRTLAEVLSR

FIG. 4c

CSQNITETQESLSSLNRELVKSRDQVHEDRSIQQIQCCLDKMNFIYKQFKKSRMRPGL
GYNEEQIHKLDKVNFSHLAKRLLQVFQEECVQKYQASLVTHGKRMRVVHETRNHLRLV
GCSVAACNTEAQGVQESLSKLLEELSHQLLQDRAKGAQASPPPIAPYPSPTRKDLLLH
MQELCEGMKLLASDLLDNNRIIERLNRVPAPPDV"

3'UTR      2478..3221

BASE COUNT  710 a   941 c   949 g   621 t

ORIGIN
    1 caccgccaca aggaggcagg gaagaaaccc actagtccca gctcctgggg tggcacagac
   61 attgcaactg gccctgcctg tgggtcctag gccctgaaag ctaccaggag gctaagaaca
  121 ctgctcatga atgacagtga gccctgaaag ctctgggggt gtcaccagt cccacaagcc
  181 tgcatcccct gcagtggaga tgggctcagc tcctgacgt gccacagaca gaaagcataa
  241 catacactcg ccaggaagag cctttgcctg actccaggca gctcagagtg tggggcagaa
  301 ggtgaccagc cagctcaggg caggagatgc agagcacagc caattaccctg tggcacacag
  361 atgacctgct ggggcagggg gccactgcca gtcttcaaca ctaccagcta ggcccgcaaac aagaaatccg
  421 gagagctggt tgctgtgaag gtttgaggtc ctgcggaagc tgaaccacca gaacatcgtc aagctctttg
  481 aggtgaggga gtttgaggtc ctgcggaagc tgaaccacca gaacatcgtc aagctctttg
  541 cggtggagga gacgggcgga agccggcaga agtactggt gatggagtac tgctccagtg
  601 ggagcctgct gagtgtgctg gagagccctg agaatgcctt agaatgcctt tgggctgcct gaggatgagt

FIG. 4d

```
 661 tcctggtggt gctgcgctgt gtggtggccg gcatgaacca cctgcgggag aacggcattg
 721 tgcatcgcga catcaagccg gggaacatca tgcgcctcgt aggggaggag gggcagagca
 781 tctacaagct gacagacttc ggcgctgccc gggagctgga tgatgatgag aagttcgtct
 841 cggtctatgg gactgaggag tacctgcatc ccgacatgta tgagcgggcg gtgcttcgaa
 901 agccccagca aaaagcgttc ggggtgactg tggatctctg gagcattgga gtgaccttgt
 961 accatgcagc cactggcagc ctgcccttca tccccttttgg tgggccacgg cggaacaagg
1021 agatcatgta ccggatcacc acggagaagc cggctggggc cattgcaggt gcccagaggc
1081 gggagaacgg gccccctggag tggagctaca ccctccccat cacctgccag ctgtcactgg
1141 ggctgcagag ccagctggtg cccatcctgg ccaacatcct ggaggtggag caggccaagt
1201 gctggggctt cgaccagttc tttgcggaga ccagtgacat cctgcagcga gttgtcgtcc
1261 atgtcttctc cctgtcccag gcagtcctgc accacatcta tatccatgcc acaacacgga
1321 tagccatttt ccaggaggcc gtgcacaagc agaccagtgt ggccccccga caccaggagt
1381 acctctttga gggtcacctc tgtgtcctcg agcccagcgt ctcagcacag cacatcgccc
1441 acacgacggc aagcagcccc ctgaccctct tcagcacagc catccctaag gggctggcct
1501 tcagggaccc tgctctggac gtccccaagt tcgtccccaa agtggacctg caggcggatt
1561 acaacactgc caagggcgtg ttgggcgccg gctaccaggc cctgcggctg cacgggccc
1621 tgctggatgg gcaggagcta atgtttcggg ggctgcactg ggtcatggag gtgctccagg
1681 ccacatgcag acggactctg gaagtggcaa ggacatccct cctctacctc agcagcagcc
1741 tgggaactga gaggttcagc agcgtggctg gaacgcctga gatccaggaa ctgaaggcgg
1801 ctgcagaact gaggtccagg ctgcggactc tagcggaggt cctctccaga tgctcccaaa
1861 atatcacgga gacccaggag agcctgagca gcctgaaccg ggagctggtg aagagccggg
1921 atcaggtaca tgaggacaga agcatccagc agattcagtg ctgtttggac aagatgaact
```

FIG. 4e

```
1981 tcatctacaa acagttcaag aagtctagga tgaggccagg gcttggctac aacgaggagc
2041 agattcacaa gctggataag gtgaatttca gtcatttagc caaaagactc ctgcaggtgt
2101 tccaggagga gtgcgtgcag aagtatcaag cgtccttagt cacacacggc aagaggatga
2161 gggtggtgca cgagaccagg aaccacctgc gcctggttgg ctgttctgtg gctgcctgta
2221 acacagaagc ccaggggtc caggagagtc tcagcaagct cctggaagag ctatctcacc
2281 agctccttca ggaccgagca aaggggctc aggcctcgcc gcctcccata gctccttacc
2341 ccagccctac acgaaggac ctgcttctcc acatgcaaga gctctgcgag gggatgaagc
2401 tgctggcatc tgacctcctg gacaacaacc gcatcatcga acggctaaat agagtcccag
2461 cacctcctga tgtctgagct ccatggggca catgaggcat cctgaagcat tagaatgatt
2521 ccaacactgc tcttctgcac catgagacca acccagggca agatcccatc ccatcacatc
2581 agcctacctc cctcctggct gctggccagg atgtcgccag cattaccttc cactgccttt
2641 ctccctggga agcagcacag ctgagactgg gcaccaggcc acctctgttg ggacccacag
2701 gaaagagtgt ggcagcaact gcctggctga cctttctatc ttctctaggc tcaggtactg
2761 ctcctccatg cccatggctg ggccgtgggg agaagaagct ctcatacgcc ttcccactcc
2821 ctctggttta taggacttca ctccctagcc aacaggagag gaggcctcct ggggtttccc
2881 cagggcagta ggtcaaacga cctcatcaca gtcttccttc ctcttcaagc gtttcatgtt
2941 gaacacagct ctctccactc ccttgtgatt tctgagggtc accactgcca gcctcaggca
3001 acatagagag cctcctgttc tttctatgct tggtctgact gagcctaaag ttgagaaaat
3061 gggtggccaa ggccagtgcc agtgtcttgg ggcccctttg gctctccctc actctctgag
3121 gctccagctg gtcctgggac atgcagccag gactgtgagt ctgggcacgt ccaaggcctg
3181 caccttcaag aagtggaata aatgtggcct ttgcttctgt t
```

FIG. 4f

FIG. 5
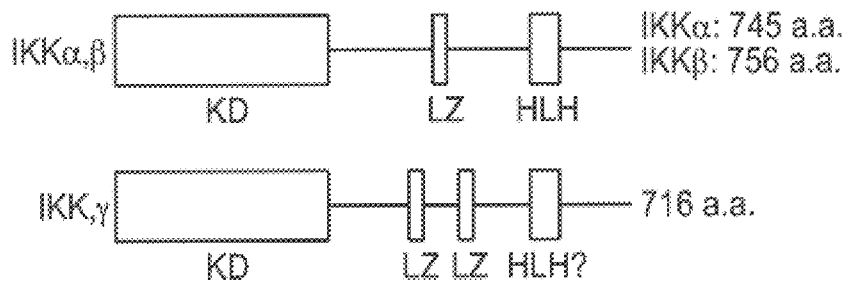
SCHEMATIC REPRESENTATION OF IKKα, β AND γ
KD, KINASE DOMAIN; LZ, LEUCINE ZIPPER; HLH, HELIX-LOOP-HELIX.
IKKγ HAS SIMILARITY TO IKKα (21.1%) AND IKKβ (22.9%) AT THE AMINO
ACID LEVEL. IKKα HAS A 51.8% SIMILARITY TO IKKβ.
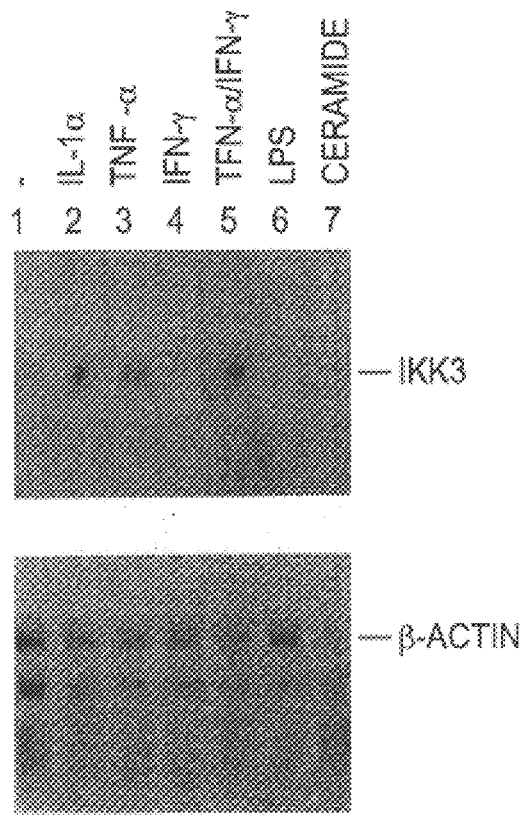
FIG. 6

NORTHERN BLOT ANALYSIS.
THE HUMAN TISSUE FILTER FOR THE NORTHERN BLOT
(GENE HUNTER, TOYOBO) WAS PROBED WITH THE
IKK3 SPECIFIC PRIMERS.

FIG. 16a

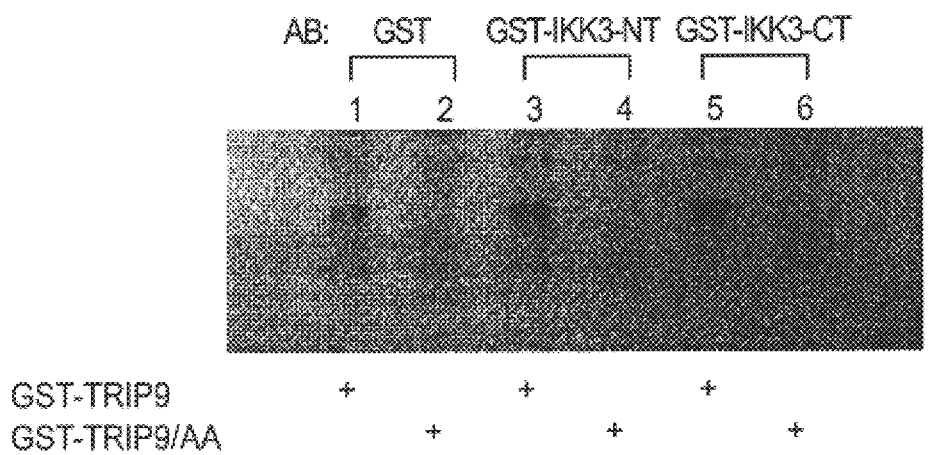

FIG. 16b

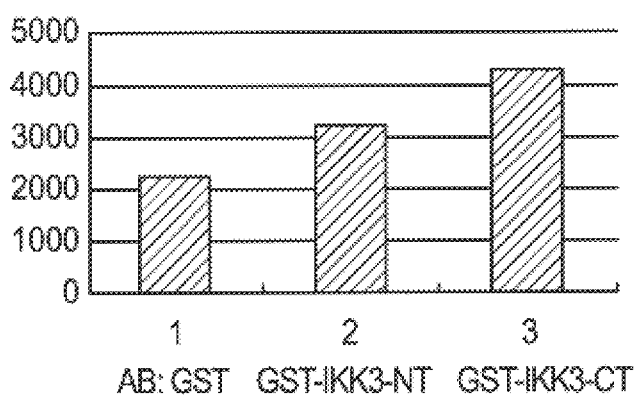

Antibody against IKK3 effect on the kinase activity of IKK3. A. The bacterially expressed GST-IKK3 were incubated with the bacterially expressed GST-TRIP9 (IkBβ), -TRIP9/AA, antibody and [γ-$^{32}$P] for the 30 minutes at 30. Proteings were separated by SDS-PAGE, stained with Coomassie blue and analyzed by autoradiography. B. IKK3 antobody activate the IKK3 kinase activity. The amount of GST-TRIP9 phosphoprotein was counted by Image analyzer (Fugi Film).

SEQUENCE LISTING

<160> NUMBER OF SEQ ID NOS: 45

<210> SEQ ID NO 1
<211> LENGTH: 3221
<212> TYPE: DNA
<213> ORGANISM: Homo sapiens
<220> FEATURE:
<221> NAME/KEY: CDS
<222> LOCATION: (327)..(2477)

<400> SEQUENCE: 1

```
caccgccaca aggaggcagg gaagaaaccc actagtccca gctcctgggg tggcacagac        60
attgcaactg gccctgcctg tgggtcctag gggcccttgg ctaccaggag gctaagaaca       120
ctgctcatga atgacagtga gccctgaaag ctctgggggt gtcacccagt cccacaagcc       180
tgcatcccct gcagtggaga tgggctcagc tcctggacgt gccacagaca gaaagcataa       240
catacactcg ccaggaagag cctttgcctg actcagggca gctcagagtg tggggcagaa       300
ggtgaccagc cagctcaggg cagga g atg cag agc aca gcc aat tac ctg tgg       353
                                Met Gln Ser Thr Ala Asn Tyr Leu Trp
                                  1               5 cac aca gat gac ctg ctg ggg cag ggg gcc act gcc agt gtg tac aag       401
His Thr Asp Asp Leu Leu Gly Gln Gly Ala Thr Ala Ser Val Tyr Lys
 10                  15                  20                  25 gcc cgc aac aag aaa tcc gga gag ctg gtt gct gtg aag gtc ttc aac       449
Ala Arg Asn Lys Lys Ser Gly Glu Leu Val Ala Val Lys Val Phe Asn
                 30                  35                  40 act acc agc tac ctg cgg ccc cgc gag gtg cag gtg agg gag ttt gag       497
Thr Thr Ser Tyr Leu Arg Pro Arg Glu Val Gln Val Arg Glu Phe Glu
             45                  50                  55 gtc ctg cgg aag ctg aac cac cag aac atc gtc aag ctc ttt gcg gtg       545
Val Leu Arg Lys Leu Asn His Gln Asn Ile Val Lys Leu Phe Ala Val
         60                  65                  70 gag gag acg ggc gga agc cgg cag aag gta ctg gtg atg gag tac tgc       593
Glu Glu Thr Gly Gly Ser Arg Gln Lys Val Leu Val Met Glu Tyr Cys
     75                  80                  85 tcc agt ggg agc ctg ctg agt gtg ctg gag agc cct gag aat gcc ttt       641
Ser Ser Gly Ser Leu Leu Ser Val Leu Glu Ser Pro Glu Asn Ala Phe
 90                  95                 100                 105 ggg ctg cct gag gat gag ttc ctg gtg gtg ctg cgc tgt gtg gtg gcc       689
Gly Leu Pro Glu Asp Glu Phe Leu Val Val Leu Arg Cys Val Val Ala
                110                 115                 120 ggc atg aac cac ctg cgg gag aac ggc att gtg cat cgc gac atc aag       737
Gly Met Asn His Leu Arg Glu Asn Gly Ile Val His Arg Asp Ile Lys
            125                 130                 135 ccg ggg aac atc atg cgc ctc gta ggg gag gag ggg cag agc atc tac       785
Pro Gly Asn Ile Met Arg Leu Val Gly Glu Glu Gly Gln Ser Ile Tyr
        140                 145                 150 aag ctg aca gac ttc ggc gct gcc cgg gag ctg gat gat gat gag aag       833
Lys Leu Thr Asp Phe Gly Ala Ala Arg Glu Leu Asp Asp Asp Glu Lys
    155                 160                 165 ttc gtc tcg gtc tat ggg act gag gag tac ctg cat ccc gac atg tat       881
Phe Val Ser Val Tyr Gly Thr Glu Glu Tyr Leu His Pro Asp Met Tyr
170                 175                 180                 185 gag cgg gcg gtg ctt cga aag ccc cag caa aaa gcg ttc ggg gtg act       929
Glu Arg Ala Val Leu Arg Lys Pro Gln Gln Lys Ala Phe Gly Val Thr
                190                 195                 200
```

```
gtg gat ctc tgg agc att gga gtg acc ttg tac cat gca gcc act ggc      977
Val Asp Leu Trp Ser Ile Gly Val Thr Leu Tyr His Ala Ala Thr Gly
        205                 210                 215 agc ctg ccc ttc atc ccc ttt ggt ggg cca cgg cgg aac aag gag atc     1025
Ser Leu Pro Phe Ile Pro Phe Gly Gly Pro Arg Arg Asn Lys Glu Ile
                220                 225                 230 atg tac cgg atc acc acg gag aag ccg gct ggg gcc att gca ggt gcc     1073
Met Tyr Arg Ile Thr Thr Glu Lys Pro Ala Gly Ala Ile Ala Gly Ala
    235                 240                 245 cag agg cgg gag aac ggg ccc ctg gag tgg agc tac acc ctc ccc atc     1121
Gln Arg Arg Glu Asn Gly Pro Leu Glu Trp Ser Tyr Thr Leu Pro Ile
250                 255                 260                 265 acc tgc cag ctg tca ctg ggg ctg cag agc cag ctg gtg ccc atc ctg     1169
Thr Cys Gln Leu Ser Leu Gly Leu Gln Ser Gln Leu Val Pro Ile Leu
                270                 275                 280 gcc aac atc ctg gag gtg gag cag gcc aag tgc tgg ggc ttc gac cag     1217
Ala Asn Ile Leu Glu Val Glu Gln Ala Lys Cys Trp Gly Phe Asp Gln
            285                 290                 295 ttc ttt gcg gag acc agt gac atc ctg cag cga gtt gtc gtc cat gtc     1265
Phe Phe Ala Glu Thr Ser Asp Ile Leu Gln Arg Val Val Val His Val
        300                 305                 310 ttc tcc ctg tcc cag gca gtc ctg cac cac atc tat atc cat gcc cac     1313
Phe Ser Leu Ser Gln Ala Val Leu His His Ile Tyr Ile His Ala His
    315                 320                 325 aac acg ata gcc att ttc cag gag gcc gtg cac aag cag acc agt gtg     1361
Asn Thr Ile Ala Ile Phe Gln Glu Ala Val His Lys Gln Thr Ser Val
330                 335                 340                 345 gcc ccc cga cac cag gag tac ctc ttt gag ggt cac ctc tgt gtc ctc     1409
Ala Pro Arg His Gln Glu Tyr Leu Phe Glu Gly His Leu Cys Val Leu
                350                 355                 360 gag ccc agc gtc tca gca cag cac atc gcc cac acg acg gca agc agc     1457
Glu Pro Ser Val Ser Ala Gln His Ile Ala His Thr Thr Ala Ser Ser
            365                 370                 375 ccc ctg acc ctc ttc agc aca gcc atc cct aag ggg ctg gcc ttc agg     1505
Pro Leu Thr Leu Phe Ser Thr Ala Ile Pro Lys Gly Leu Ala Phe Arg
        380                 385                 390 gac cct gct ctg gac gtc ccc aag ttc gtc ccc aaa gtg gac ctg cag     1553
Asp Pro Ala Leu Asp Val Pro Lys Phe Val Pro Lys Val Asp Leu Gln
    395                 400                 405 gcg gat tac aac act gcc aag ggc gtg ttg ggc gcc ggc tac cag gcc     1601
Ala Asp Tyr Asn Thr Ala Lys Gly Val Leu Gly Ala Gly Tyr Gln Ala
410                 415                 420                 425 ctg cgg ctg gca cgg gcc ctg ctg gat ggg cag gag cta atg ttt cgg     1649
Leu Arg Leu Ala Arg Ala Leu Leu Asp Gly Gln Glu Leu Met Phe Arg
                430                 435                 440 ggg ctg cac tgg gtc atg gag gtg ctc cag gcc aca tgc aga cgg act     1697
Gly Leu His Trp Val Met Glu Val Leu Gln Ala Thr Cys Arg Arg Thr
            445                 450                 455 ctg gaa gtg gca agg aca tcc ctc ctc tac ctc agc agc agc ctg gga     1745
Leu Glu Val Ala Arg Thr Ser Leu Leu Tyr Leu Ser Ser Ser Leu Gly
        460                 465                 470 act gag agg ttc agc agc gtg gct gga acg cct gag atc cag gaa ctg     1793
Thr Glu Arg Phe Ser Ser Val Ala Gly Thr Pro Glu Ile Gln Glu Leu
    475                 480                 485 aag gcg gct gca gaa ctg agg tcc agg ctg cgg act cta gcg gag gtc     1841
Lys Ala Ala Ala Glu Leu Arg Ser Arg Leu Arg Thr Leu Ala Glu Val
490                 495                 500                 505 ctc tcc aga tgc tcc caa aat atc acg gag acc cag gag agc ctg agc     1889
Leu Ser Arg Cys Ser Gln Asn Ile Thr Glu Thr Gln Glu Ser Leu Ser
                510                 515                 520
```

-continued

| | |
|---|---|
| agc ctg aac cgg gag ctg gtg aag agc cgg gat cag gta cat gag gac<br>Ser Leu Asn Arg Glu Leu Val Lys Ser Arg Asp Gln Val His Glu Asp<br>525 530 535 | 1937 |
| aga agc atc cag cag att cag tgc tgt ttg gac aag atg aac ttc atc<br>Arg Ser Ile Gln Gln Ile Gln Cys Cys Leu Asp Lys Met Asn Phe Ile<br>540 545 550 | 1985 |
| tac aaa cag ttc aag aag tct agg atg agg cca ggg ctt ggc tac aac<br>Tyr Lys Gln Phe Lys Lys Ser Arg Met Arg Pro Gly Leu Gly Tyr Asn<br>555 560 565 | 2033 |
| gag gag cag att cac aag ctg gat aag gtg aat ttc agt cat tta gcc<br>Glu Glu Gln Ile His Lys Leu Asp Lys Val Asn Phe Ser His Leu Ala<br>570 575 580 585 | 2081 |
| aaa aga ctc ctg cag gtg ttc cag gag gag tgc gtg cag aag tat caa<br>Lys Arg Leu Leu Gln Val Phe Gln Glu Glu Cys Val Gln Lys Tyr Gln<br>590 595 600 | 2129 |
| gcg tcc tta gtc aca cac ggc aag agg atg agg gtg gtg cac gag acc<br>Ala Ser Leu Val Thr His Gly Lys Arg Met Arg Val Val His Glu Thr<br>605 610 615 | 2177 |
| agg aac cac ctg cgc ctg gtt ggc tgt tct gtg gct gcc tgt aac aca<br>Arg Asn His Leu Arg Leu Val Gly Cys Ser Val Ala Ala Cys Asn Thr<br>620 625 630 | 2225 |
| gaa gcc cag ggg gtc cag gag agt ctc agc aag ctc ctg gaa gag cta<br>Glu Ala Gln Gly Val Gln Glu Ser Leu Ser Lys Leu Leu Glu Glu Leu<br>635 640 645 | 2273 |
| tct cac cag ctc ctt cag gac cga gca aag ggg gct cag gcc tcg ccg<br>Ser His Gln Leu Leu Gln Asp Arg Ala Lys Gly Ala Gln Ala Ser Pro<br>650 655 660 665 | 2321 |
| cct ccc ata gct cct tac ccc agc cct aca cga aag gac ctg ctt ctc<br>Pro Pro Ile Ala Pro Tyr Pro Ser Pro Thr Arg Lys Asp Leu Leu Leu<br>670 675 680 | 2369 |
| cac atg caa gag ctc tgc gag ggg atg aag ctg ctg gca tct gac ctc<br>His Met Gln Glu Leu Cys Glu Gly Met Lys Leu Leu Ala Ser Asp Leu<br>685 690 695 | 2417 |
| ctg gac aac aac cgc atc atc gaa cgg cta aat aga gtc cca gca cct<br>Leu Asp Asn Asn Arg Ile Ile Glu Arg Leu Asn Arg Val Pro Ala Pro<br>700 705 710 | 2465 |
| cct gat gtc tga gctccatggg gcacatgagg catcctgaag cattagaatg<br>Pro Asp Val<br>715 | 2517 |
| attccaacac tgctcttctg caccatgaga ccaacccagg gcaagatccc atcccatcac | 2577 |
| atcagcctac ctccctcctg gctgctggcc aggatgtcgc cagcattacc ttccactgcc | 2637 |
| tttctccctg ggaagcagca cagctgagac tgggcaccag gccacctctg ttgggaccca | 2697 |
| caggaaagag tgtggcagca actgcctggc tgacctttct atcttctcta ggctcaggta | 2757 |
| ctgctcctcc atgcccatgg ctgggccgtg gggagaagaa gctctcatac gccttcccac | 2817 |
| tccctctggt ttataggact tcactcccta gccaacagga gaggaggcct cctggggttt | 2877 |
| ccccagggca gtaggtcaaa cgacctcatc acagtcttcc ttcctcttca agcgtttcat | 2937 |
| gttgaacaca gctctctcca ctcccttgtg atttctgagg gtcaccactg ccagcctcag | 2997 |
| gcaacataga gagcctcctg ttctttctat gcttggtctg actgagccta agttgagaa | 3057 |
| aatgggtggc caaggccagt gccagtgtct tggggcccct ttggctctcc ctcactctct | 3117 |
| gaggctccag ctggtcctgg gacatgcagc caggactgtg agtctgggca cgtccaaggc | 3177 |
| ctgcaccttc aagaagtgga ataaatgtgg cctttgcttc tgtt | 3221 |

```
<210> SEQ ID NO 2
<211> LENGTH: 716
<212> TYPE: PRT
<213> ORGANISM: Homo sapiens

<400> SEQUENCE: 2

Met Gln Ser Thr Ala Asn Tyr Leu Trp His Thr Asp Asp Leu Leu Gly
 1               5                  10                  15

Gln Gly Ala Thr Ala Ser Val Tyr Lys Ala Arg Asn Lys Lys Ser Gly
             20                  25                  30

Glu Leu Val Ala Val Lys Val Phe Asn Thr Thr Ser Tyr Leu Arg Pro
         35                  40                  45

Arg Glu Val Gln Val Arg Glu Phe Glu Val Leu Arg Lys Leu Asn His
     50                  55                  60

Gln Asn Ile Val Lys Leu Phe Ala Val Glu Glu Thr Gly Gly Ser Arg
 65                  70                  75                  80

Gln Lys Val Leu Val Met Glu Tyr Cys Ser Ser Gly Ser Leu Leu Ser
                 85                  90                  95

Val Leu Glu Ser Pro Glu Asn Ala Phe Gly Leu Pro Glu Asp Glu Phe
            100                 105                 110

Leu Val Val Leu Arg Cys Val Val Ala Gly Met Asn His Leu Arg Glu
        115                 120                 125

Asn Gly Ile Val His Arg Asp Ile Lys Pro Gly Asn Ile Met Arg Leu
    130                 135                 140

Val Gly Glu Glu Gly Gln Ser Ile Tyr Lys Leu Thr Asp Phe Gly Ala
145                 150                 155                 160

Ala Arg Glu Leu Asp Asp Asp Glu Lys Phe Val Ser Val Tyr Gly Thr
                165                 170                 175

Glu Glu Tyr Leu His Pro Asp Met Tyr Glu Arg Ala Val Leu Arg Lys
            180                 185                 190

Pro Gln Gln Lys Ala Phe Gly Val Thr Val Asp Leu Trp Ser Ile Gly
        195                 200                 205

Val Thr Leu Tyr His Ala Ala Thr Gly Ser Leu Pro Phe Ile Pro Phe
    210                 215                 220

Gly Gly Pro Arg Arg Asn Lys Glu Ile Met Tyr Arg Ile Thr Thr Glu
225                 230                 235                 240

Lys Pro Ala Gly Ala Ile Ala Gly Ala Gln Arg Arg Glu Asn Gly Pro
                245                 250                 255

Leu Glu Trp Ser Tyr Thr Leu Pro Ile Thr Cys Gln Leu Ser Leu Gly
            260                 265                 270

Leu Gln Ser Gln Leu Val Pro Ile Leu Ala Asn Ile Leu Glu Val Glu
        275                 280                 285

Gln Ala Lys Cys Trp Gly Phe Asp Gln Phe Phe Ala Glu Thr Ser Asp
    290                 295                 300

Ile Leu Gln Arg Val Val Val His Val Phe Ser Leu Ser Gln Ala Val
305                 310                 315                 320

Leu His His Ile Tyr Ile His Ala His Asn Thr Ile Ala Ile Phe Gln
                325                 330                 335

Glu Ala Val His Lys Gln Thr Ser Val Ala Pro Arg His Gln Glu Tyr
            340                 345                 350

Leu Phe Glu Gly His Leu Cys Val Leu Glu Pro Ser Val Ser Ala Gln
        355                 360                 365

His Ile Ala His Thr Thr Ala Ser Ser Pro Leu Thr Leu Phe Ser Thr
    370                 375                 380
```

```
Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
            405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
            435                 440                 445

Val Leu Gln Ala Thr Cys Arg Arg Thr Leu Glu Val Ala Arg Thr Ser
450                 455                 460

Leu Leu Tyr Leu Ser Ser Leu Gly Thr Glu Arg Phe Ser Ser Val
465                 470                 475                 480

Ala Gly Thr Pro Glu Ile Gln Glu Leu Lys Ala Ala Ala Glu Leu Arg
                485                 490                 495

Ser Arg Leu Arg Thr Leu Ala Glu Val Leu Ser Arg Cys Ser Gln Asn
            500                 505                 510

Ile Thr Glu Thr Gln Glu Ser Leu Ser Ser Leu Asn Arg Glu Leu Val
            515                 520                 525

Lys Ser Arg Asp Gln Val His Glu Asp Arg Ser Ile Gln Gln Ile Gln
530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
            565                 570                 575

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
            595                 600                 605

Lys Arg Met Arg Val Val His Glu Thr Arg Asn His Leu Arg Leu Val
610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
                645                 650                 655

Arg Ala Lys Gly Ala Gln Ala Ser Pro Pro Ile Ala Pro Tyr Pro
            660                 665                 670

Ser Pro Thr Arg Lys Asp Leu Leu His Met Gln Glu Leu Cys Glu
            675                 680                 685

Gly Met Lys Leu Leu Ala Ser Asp Leu Leu Asp Asn Asn Arg Ile Ile
            690                 695                 700

Glu Arg Leu Asn Arg Val Pro Ala Pro Pro Asp Val
705                 710                 715

<210> SEQ ID NO 3
<211> LENGTH: 745
<212> TYPE: PRT
<213> ORGANISM: Homo sapiens

<400> SEQUENCE: 3

Met Glu Arg Pro Pro Gly Leu Arg Pro Gly Ala Gly Gly Pro Trp Glu
 1               5                  10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45
```

-continued

```
Glu Leu Ser Thr Lys Asn Arg Glu Arg Trp Cys His Glu Ile Gln Ile
     50                  55                  60

Met Lys Lys Leu Asn His Ala Asn Val Val Lys Ala Cys Asp Val Pro
 65                  70                  75                  80

Glu Glu Leu Asn Ile Leu Ile His Asp Val Pro Leu Leu Ala Met Glu
                 85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
            115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
                180                 185                 190

Phe Glu Asn Lys Pro Tyr Thr Ala Thr Val Asp Tyr Trp Ser Phe Gly
            195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
                260                 265                 270

Glu Asn Trp Leu Gln Leu Met Leu Asn Trp Asp Pro Gln Gln Arg Gly
            275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
            355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
    435                 440                 445

Arg Ala Ala Met Leu Ser Leu Leu Arg Tyr Asn Ala Asn Leu Thr Lys
450                 455                 460
```

```
Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
                500                 505                 510

Glu Met Glu Glu Lys Ala Ile His Tyr Ala Glu Val Gly Val Ile Gly
            515                 520                 525

Tyr Leu Glu Asp Gln Ile Met Ser Leu His Ala Glu Ile Met Glu Leu
            530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
                580                 585                 590

Thr Val Gln Ser Gln Asp Arg Val Leu Lys Glu Leu Phe Gly His Leu
            595                 600                 605

Ser Lys Leu Leu Gly Cys Lys Gln Lys Ile Ile Asp Leu Leu Pro Lys
610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
                660                 665                 670

Gly Ala Val Thr Pro Gln Thr Ser Ala Trp Leu Pro Pro Thr Ser Ala
            675                 680                 685

Glu His Asp His Ser Leu Ser Cys Val Val Thr Pro Gln Asp Gly Glu
            690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
                740                 745

<210> SEQ ID NO 4
<211> LENGTH: 756
<212> TYPE: PRT
<213> ORGANISM: Homo sapiens

<400> SEQUENCE: 4

Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95
```

-continued

```
Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
            115                 120                 125

Ile Ala Ser Ala Leu Arg Tyr Leu His Glu Asn Arg Ile Ile His Arg
            130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
            195                 200                 205

Gly Thr Leu Ala Phe Glu Cys Ile Thr Gly Phe Arg Pro Phe Leu Pro
            210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
            275                 280                 285

Gly Thr Asp Pro Thr Tyr Gly Pro Asn Gly Cys Phe Lys Ala Leu Asp
            290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
            355                 360                 365

Gln Cys Ile Ser Asp Gly Lys Leu Asn Glu Gly His Thr Leu Asp Met
370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415

Pro Lys Arg Asn Leu Ala Phe Phe Gln Leu Arg Lys Val Trp Gly Gln
            420                 425                 430

Val Trp His Ser Ile Gln Thr Leu Lys Glu Asp Cys Asn Arg Leu Gln
            435                 440                 445

Gln Gly Gln Arg Ala Ala Met Met Asn Leu Leu Arg Asn Asn Ser Cys
            450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510
```

```
Ala Trp Arg Glu Met Glu Gln Ala Val Glu Leu Cys Gly Arg Glu Asn
            515                 520                 525

Glu Val Lys Leu Leu Val Glu Arg Met Met Ala Leu Gln Thr Asp Ile
        530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
        675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720

Asn Ala Ile Gln Asp Thr Val Arg Glu Gln Asp Ser Phe Thr Ala
                725                 730                 735

Leu Asp Trp Ser Trp Leu Gln Thr Glu Glu Glu His Ser Cys Leu
            740                 745                 750

Glu Gln Ala Ser
        755

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
tcctgatttc tgcagctctg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
aacttctcca caaccctctg                                              20

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Primer
```

```
<400> SEQUENCE: 7 cccccgcgg ccgccaccat gcagagcaca gccaattacc tgtgg                45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 8 cccccgcgg ccgcctcaga catcaggagg tgctgggact ctatt                45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 9 cccccgcgg ccgccatgga gcggccccg gggctgcggc cgggc                 45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 10 cccccgcgg ccgcctcatt ctgttaacca actccaatca agatt                45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 11 cccccgcgg ccgccatgag ctggtcacct tccctgacaa cgcag                45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 12 cccccgcgg ccgcctcatg aggcctgctc caggcagctg tgctc                45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 13 cccccgcgg ccgccatgtt ccaggcggcc gagcgcccccc aggag               45

<210> SEQ ID NO 14
<211> LENGTH: 45
```

```
<212> TYPE: DNA
<213> ORGANISM: Artificial Sequence
<220> FEATURE:
<223> OTHER INFORMATION: Description of Artificial Sequence: Primer

<400> SEQUENCE: 14 cccccgcgg ccgcctcaga ggcggatctc ctgcagctcc ttgac            45

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 15 cccccgcgg ccgccatggc cggggtcgcg tgcttgggga aaact            45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 16 cccccgcgg ccgcctcaca gctctgggcc aagctctgcg cccag            45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 17 cccccgcgg ccgccatggc tggggtcgcg tgcttgggaa aagct            45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 18 cccccgcgg ccgcctcaca gccccgggcc caactccgcg cccaa            45

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 19 cccccgcgg ccgcatgtcg gaggcgcgga aggggccgga cgag             44

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Primer
```

```
<400> SEQUENCE: 20 cccccccgcgg ccgcctcaca gcgcccccac gtgggggagt ggcag          45

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 21
gagctggttg ctgtgatggt cttcaacact acc                        33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 22
ggtagtgttg aagaccatca cagcaaccag ctc                        33

<210> SEQ ID NO 23
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 23
agtgggagcc tgctggctgt rgctggaggc tcctgagaat gcctttt         46

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 24
aaagcattct caggagcctc cagcacagcc agcaggctcc cact            44

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 25
gagctggatg atgatgcgaa gttcgtcgcg gtctatggga ctgag           45

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 26
ctcagtccca tagaccgcga cgaacttcga tcatcatcca gctc            44

<210> SEQ ID NO 27
<211> LENGTH: 45
```

```
<212> TYPE: DNA
<213> ORGANISM: Artificial Sequence
<220> FEATURE:
<223> OTHER INFORMATION: Description of Artificial Sequence: Primer

<400> SEQUENCE: 27
agtgggagcc tgctggaggt gctggaggag cctgagaatg ccttt          45

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 28
aaaggcattc tcaggctcct ccagcacctc cagcaggctc ccact          45

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 29
gatgagaagt tcgtcgaggt ctatgggact gag                       33

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 30
ctcagtccca tagacctcga cgaacttctc atc                       33

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 31
gacgaccgcc acgacgccgg cctggacgcc atgaaagacg aggag          45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 32
ctcctcgtct ttcatggcgt ccaggccggc gtcgtggcgg tcgtc          45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 33
gatgaatggt gcgacgccgg cctgggcgct ctaggtcccg acgca          45

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 34
tgcgtcggga cctagagcgc ccaggccggc gtcgcaccat tcatc          45

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 35
gatgaatggt gcgacgccgc ctgggcgccc tgggtccgga cgca           44

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 36
tgcgtccgga cccagggcgc ccaggccggc gtcgcaccat tcatc          45

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 37
gagagccagt accacgctgg cattgaggct ctgcgctctc tgcgc          45

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 38
gcgcagagag cgcagagcct caatgccagc gtcgtactgg ctctc          45

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 39
ggggagcggg ctgatgccac ctatggcgcc tcctcgctca cctac          45

<210> SEQ ID NO 40
<211> LENGTH: 45
```

```
<212> TYPE: DNA
<213> ORGANISM: Artificial Sequence
<220> FEATURE:
<223> OTHER INFORMATION: Description of Artificial Sequence: Primer

<400> SEQUENCE: 40
gtaggtgagc gaggaggcgc cataggtggc atcagcccgc tcccc            45

<210> SEQ ID NO 41
<211> LENGTH: 716
<212> TYPE: PRT
<213> ORGANISM: Artificial Sequence
<220> FEATURE:
<223> OTHER INFORMATION: Description of Artificial Sequence: DT7-IKK3
      mutant

<400> SEQUENCE: 41
```

| Met | Gln | Ser | Thr | Ala | Asn | Tyr | Leu | Trp | His | Thr | Asp | Asp | Leu | Leu | Gly |
|---|---|---|---|---|---|---|---|---|---|---|---|---|---|---|---|
| 1 | | | | 5 | | | | | 10 | | | | | 15 | |

| Gln | Gly | Ala | Thr | Ala | Ser | Val | Tyr | Lys | Ala | Arg | Asn | Lys | Lys | Ser | Gly |
|---|---|---|---|---|---|---|---|---|---|---|---|---|---|---|---|
| | | | 20 | | | | | 25 | | | | | 30 | | |

| Glu | Leu | Val | Ala | Val | Met | Val | Phe | Asn | Thr | Thr | Ser | Tyr | Leu | Arg | Pro |
|---|---|---|---|---|---|---|---|---|---|---|---|---|---|---|---|
| | | 35 | | | | | 40 | | | | | 45 | | | |

| Arg | Glu | Val | Gln | Val | Arg | Glu | Phe | Glu | Val | Leu | Arg | Lys | Leu | Asn | His |
|---|---|---|---|---|---|---|---|---|---|---|---|---|---|---|---|
| | 50 | | | | | 55 | | | | | 60 | | | | |

| Gln | Asn | Ile | Val | Lys | Leu | Phe | Ala | Val | Glu | Glu | Thr | Gly | Gly | Ser | Arg |
|---|---|---|---|---|---|---|---|---|---|---|---|---|---|---|---|
| 65 | | | | | 70 | | | | | 75 | | | | | 80 |

| Gln | Lys | Val | Leu | Val | Met | Glu | Tyr | Cys | Ser | Gly | Ser | Leu | Leu | Ser | 
|---|---|---|---|---|---|---|---|---|---|---|---|---|---|---|
| | | | | 85 | | | | | 90 | | | | | 95 |

| Val | Leu | Glu | Ser | Pro | Glu | Asn | Ala | Phe | Gly | Leu | Pro | Glu | Asp | Glu | Phe |
|---|---|---|---|---|---|---|---|---|---|---|---|---|---|---|---|
| | | | | 100 | | | | | 105 | | | | | 110 | |

| Leu | Val | Val | Leu | Arg | Cys | Val | Val | Ala | Gly | Met | Asn | His | Leu | Arg | Glu |
|---|---|---|---|---|---|---|---|---|---|---|---|---|---|---|---|
| | | | 115 | | | | | 120 | | | | | 125 | | |

| Asn | Gly | Ile | Val | His | Arg | Asp | Ile | Lys | Pro | Gly | Asn | Ile | Met | Arg | Leu |
|---|---|---|---|---|---|---|---|---|---|---|---|---|---|---|---|
| | 130 | | | | | 135 | | | | | 140 | | | | |

| Val | Gly | Glu | Glu | Gly | Gln | Ser | Ile | Tyr | Lys | Leu | Thr | Asp | Phe | Gly | Ala |
|---|---|---|---|---|---|---|---|---|---|---|---|---|---|---|---|
| 145 | | | | | 150 | | | | | 155 | | | | | 160 |

| Ala | Arg | Glu | Leu | Asp | Asp | Asp | Glu | Lys | Phe | Val | Ser | Val | Tyr | Gly | Thr |
|---|---|---|---|---|---|---|---|---|---|---|---|---|---|---|---|
| | | | | 165 | | | | | 170 | | | | | 175 | |

| Glu | Glu | Tyr | Leu | His | Pro | Asp | Met | Tyr | Glu | Arg | Ala | Val | Leu | Arg | Lys |
|---|---|---|---|---|---|---|---|---|---|---|---|---|---|---|---|
| | | | 180 | | | | | 185 | | | | | 190 | | |

| Pro | Gln | Gln | Lys | Ala | Phe | Gly | Val | Thr | Val | Asp | Leu | Trp | Ser | Ile | Gly |
|---|---|---|---|---|---|---|---|---|---|---|---|---|---|---|---|
| | | 195 | | | | | 200 | | | | | 205 | | | |

| Val | Thr | Leu | Tyr | His | Ala | Ala | Thr | Gly | Ser | Leu | Pro | Phe | Ile | Pro | Phe |
|---|---|---|---|---|---|---|---|---|---|---|---|---|---|---|---|
| | 210 | | | | | 215 | | | | | 220 | | | | |

| Gly | Gly | Pro | Arg | Arg | Asn | Lys | Glu | Ile | Met | Tyr | Arg | Ile | Thr | Thr | Glu |
|---|---|---|---|---|---|---|---|---|---|---|---|---|---|---|---|
| 225 | | | | | 230 | | | | | 235 | | | | | 240 |

| Lys | Pro | Ala | Gly | Ala | Ile | Ala | Gly | Ala | Gln | Arg | Arg | Glu | Asn | Gly | Pro |
|---|---|---|---|---|---|---|---|---|---|---|---|---|---|---|---|
| | | | | 245 | | | | | 250 | | | | | 255 | |

| Leu | Glu | Trp | Ser | Tyr | Thr | Leu | Pro | Ile | Thr | Cys | Gln | Leu | Ser | Leu | Gly |
|---|---|---|---|---|---|---|---|---|---|---|---|---|---|---|---|
| | | | 260 | | | | | 265 | | | | | 270 | | |

| Leu | Gln | Ser | Gln | Leu | Val | Pro | Ile | Leu | Ala | Asn | Ile | Leu | Glu | Val | Glu |
|---|---|---|---|---|---|---|---|---|---|---|---|---|---|---|---|
| | | 275 | | | | | 280 | | | | | 285 | | | |

| Gln | Ala | Lys | Cys | Trp | Gly | Phe | Asp | Gln | Phe | Phe | Ala | Glu | Thr | Ser | Asp |
|---|---|---|---|---|---|---|---|---|---|---|---|---|---|---|---|
| | 290 | | | | | 295 | | | | | 300 | | | | |

| Ile | Leu | Gln | Arg | Val | Val | Val | His | Val | Phe | Ser | Leu | Ser | Gln | Ala | Val |
|---|---|---|---|---|---|---|---|---|---|---|---|---|---|---|---|
| 305 | | | | | 310 | | | | | 315 | | | | | 320 |

Leu His His Ile Tyr Ile His Ala His Asn Thr Ile Ala Ile Phe Gln
            325                 330                 335

Glu Ala Val His Lys Gln Thr Ser Val Ala Pro Arg His Gln Glu Tyr
            340                 345                 350

Leu Phe Glu Gly His Leu Cys Val Leu Glu Pro Ser Val Ser Ala Gln
            355                 360                 365

His Ile Ala His Thr Thr Ala Ser Ser Pro Leu Thr Leu Phe Ser Thr
            370                 375                 380

Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
            405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
            435                 440                 445

Val Leu Gln Ala Thr Cys Arg Arg Thr Leu Glu Val Ala Arg Thr Ser
            450                 455                 460

Leu Leu Tyr Leu Ser Ser Ser Leu Gly Thr Glu Arg Phe Ser Ser Val
465                 470                 475                 480

Ala Gly Thr Pro Glu Ile Gln Glu Leu Lys Ala Ala Glu Leu Arg
            485                 490                 495

Ser Arg Leu Arg Thr Leu Ala Glu Val Leu Ser Arg Cys Ser Gln Asn
            500                 505                 510

Ile Thr Glu Thr Gln Glu Ser Leu Ser Ser Leu Asn Arg Glu Leu Val
            515                 520                 525

Lys Ser Arg Asp Gln Val His Glu Asp Arg Ser Ile Gln Gln Ile Gln
            530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
            565                 570                 575

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
            595                 600                 605

Lys Arg Met Arg Val Val His Glu Thr Arg Asn His Leu Arg Leu Val
            610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
            645                 650                 655

Arg Ala Lys Gly Ala Gln Ala Ser Pro Pro Ile Ala Pro Tyr Pro
            660                 665                 670

Ser Pro Thr Arg Lys Asp Leu Leu His Met Gln Glu Leu Cys Glu
            675                 680                 685

Gly Met Lys Leu Leu Ala Ser Asp Leu Leu Asp Asn Asn Arg Ile Ile
            690                 695                 700

Glu Arg Leu Asn Arg Val Pro Ala Pro Pro Asp Val
705                 710                 715

<210> SEQ ID NO 42
<211> LENGTH: 716
<212> TYPE: PRT

<213> ORGANISM: Artificial Sequence
<220> FEATURE:
<223> OTHER INFORMATION: Description of Artificial Sequence: DT7-IKK3 mutant

<400> SEQUENCE: 42

```
Met Gln Ser Thr Ala Asn Tyr Leu Trp His Thr Asp Asp Leu Leu Gly
 1               5                  10                  15

Gln Gly Ala Thr Ala Ser Val Tyr Lys Ala Arg Asn Lys Lys Ser Gly
            20                  25                  30

Glu Leu Val Ala Val Lys Val Phe Asn Thr Thr Ser Tyr Leu Arg Pro
        35                  40                  45

Arg Glu Val Gln Val Arg Glu Phe Glu Val Leu Arg Lys Leu Asn His
    50                  55                  60

Gln Asn Ile Val Lys Leu Phe Ala Val Glu Glu Thr Gly Gly Ser Arg
65                  70                  75                  80

Gln Lys Val Leu Val Met Glu Tyr Cys Ser Ser Gly Ser Leu Leu Ala
                85                  90                  95

Val Leu Glu Ala Pro Glu Asn Ala Phe Gly Leu Pro Glu Asp Glu Phe
            100                 105                 110

Leu Val Leu Arg Cys Val Val Ala Gly Met Asn His Leu Arg Glu
        115                 120                 125

Asn Gly Ile Val His Arg Asp Ile Lys Pro Gly Asn Ile Met Arg Leu
    130                 135                 140

Val Gly Glu Glu Gly Gln Ser Ile Tyr Lys Leu Thr Asp Phe Gly Ala
145                 150                 155                 160

Ala Arg Glu Leu Asp Asp Asp Glu Lys Phe Val Ser Val Tyr Gly Thr
                165                 170                 175

Glu Glu Tyr Leu His Pro Asp Met Tyr Glu Arg Ala Val Leu Arg Lys
            180                 185                 190

Pro Gln Gln Lys Ala Phe Gly Val Thr Val Asp Leu Trp Ser Ile Gly
        195                 200                 205

Val Thr Leu Tyr His Ala Ala Thr Gly Ser Leu Pro Phe Ile Pro Phe
    210                 215                 220

Gly Gly Pro Arg Arg Asn Lys Glu Ile Met Tyr Arg Ile Thr Thr Glu
225                 230                 235                 240

Lys Pro Ala Gly Ala Ile Ala Gly Ala Gln Arg Arg Glu Asn Gly Pro
                245                 250                 255

Leu Glu Trp Ser Tyr Thr Leu Pro Ile Thr Cys Gln Leu Ser Leu Gly
            260                 265                 270

Leu Gln Ser Gln Leu Val Pro Ile Leu Ala Asn Ile Leu Glu Val Glu
        275                 280                 285

Gln Ala Lys Cys Trp Gly Phe Asp Gln Phe Phe Ala Glu Thr Ser Asp
    290                 295                 300

Ile Leu Gln Arg Val Val Val His Val Phe Ser Leu Ser Gln Ala Val
305                 310                 315                 320

Leu His His Ile Tyr Ile His Ala His Asn Thr Ile Ala Ile Phe Gln
                325                 330                 335

Glu Ala Val His Lys Gln Thr Ser Val Ala Pro Arg His Gln Glu Tyr
            340                 345                 350

Leu Phe Glu Gly His Leu Cys Val Leu Glu Pro Ser Val Ser Ala Gln
        355                 360                 365

His Ile Ala His Thr Thr Ala Ser Ser Pro Leu Thr Leu Phe Ser Thr
    370                 375                 380
```

-continued

```
Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
            405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
        435                 440                 445

Val Leu Gln Ala Thr Cys Arg Arg Thr Leu Glu Val Ala Arg Thr Ser
    450                 455                 460

Leu Leu Tyr Leu Ser Ser Leu Gly Thr Glu Arg Phe Ser Ser Val
465                 470                 475                 480

Ala Gly Thr Pro Glu Ile Gln Glu Leu Lys Ala Ala Glu Leu Arg
                485                 490                 495

Ser Arg Leu Arg Thr Leu Ala Glu Val Leu Ser Arg Cys Ser Gln Asn
            500                 505                 510

Ile Thr Glu Thr Gln Glu Ser Leu Ser Ser Leu Asn Arg Glu Leu Val
            515                 520                 525

Lys Ser Arg Asp Gln Val His Glu Asp Arg Ser Ile Gln Gln Ile Gln
530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
                565                 570                 575

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
        595                 600                 605

Lys Arg Met Arg Val Val His Glu Thr Arg Asn His Leu Arg Leu Val
610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
                645                 650                 655

Arg Ala Lys Gly Ala Gln Ala Ser Pro Pro Ile Ala Pro Tyr Pro
            660                 665                 670

Ser Pro Thr Arg Lys Asp Leu Leu Leu His Met Gln Glu Leu Cys Glu
            675                 680                 685

Gly Met Lys Leu Leu Ala Ser Asp Leu Leu Asp Asn Asn Arg Ile Ile
        690                 695                 700

Glu Arg Leu Asn Arg Val Pro Ala Pro Pro Asp Val
705                 710                 715
```

<210> SEQ ID NO 43
<211> LENGTH: 716
<212> TYPE: PRT
<213> ORGANISM: Artificial Sequence
<220> FEATURE:
<223> OTHER INFORMATION: Description of Artificial Sequence: DT7-IKK3 mutant

<400> SEQUENCE: 43

```
Met Gln Ser Thr Ala Asn Tyr Leu Trp His Thr Asp Asp Leu Leu Gly
 1               5                  10                  15

Gln Gly Ala Thr Ala Ser Val Tyr Lys Ala Arg Asn Lys Lys Ser Gly
            20                  25                  30
```

-continued

```
Glu Leu Val Ala Val Lys Val Phe Asn Thr Thr Ser Tyr Leu Arg Pro
         35                  40                  45

Arg Glu Val Gln Val Arg Glu Phe Glu Val Leu Arg Lys Leu Asn His
     50                  55                  60

Gln Asn Ile Val Lys Leu Phe Ala Val Glu Glu Thr Gly Gly Ser Arg
 65                  70                  75                  80

Gln Lys Val Leu Val Met Glu Tyr Cys Ser Ser Gly Ser Leu Leu Ser
                 85                  90                  95

Val Leu Glu Ser Pro Glu Asn Ala Phe Gly Leu Pro Glu Asp Glu Phe
             100                 105                 110

Leu Val Val Leu Arg Cys Val Ala Gly Met Asn His Leu Arg Glu
             115                 120                 125

Asn Gly Ile Val His Arg Asp Ile Lys Pro Gly Asn Ile Met Arg Leu
130                 135                 140

Val Gly Glu Glu Gly Gln Ser Ile Tyr Lys Leu Thr Asp Phe Gly Ala
145                 150                 155                 160

Ala Arg Glu Leu Asp Asp Ala Lys Phe Val Ala Val Tyr Gly Thr
             165                 170                 175

Glu Glu Tyr Leu His Pro Asp Met Tyr Glu Arg Ala Val Leu Arg Lys
             180                 185                 190

Pro Gln Gln Lys Ala Phe Gly Val Thr Val Asp Leu Trp Ser Ile Gly
         195                 200                 205

Val Thr Leu Tyr His Ala Ala Thr Gly Ser Leu Pro Phe Ile Pro Phe
210                 215                 220

Gly Gly Pro Arg Arg Asn Lys Glu Ile Met Tyr Arg Ile Thr Thr Glu
225                 230                 235                 240

Lys Pro Ala Gly Ala Ile Ala Gly Ala Gln Arg Arg Glu Asn Gly Pro
             245                 250                 255

Leu Glu Trp Ser Tyr Thr Leu Pro Ile Thr Cys Gln Leu Ser Leu Gly
             260                 265                 270

Leu Gln Ser Gln Leu Val Pro Ile Leu Ala Asn Ile Leu Glu Val Glu
         275                 280                 285

Gln Ala Lys Cys Trp Gly Phe Asp Gln Phe Phe Ala Glu Thr Ser Asp
         290                 295                 300

Ile Leu Gln Arg Val Val His Val Phe Ser Leu Ser Gln Ala Val
305                 310                 315                 320

Leu His His Ile Tyr Ile His Ala His Asn Thr Ile Ala Ile Phe Gln
                 325                 330                 335

Glu Ala Val His Lys Gln Thr Ser Val Ala Pro Arg His Gln Glu Tyr
             340                 345                 350

Leu Phe Glu Gly His Leu Cys Val Leu Glu Pro Ser Val Ser Ala Gln
             355                 360                 365

His Ile Ala His Thr Thr Ala Ser Ser Pro Leu Thr Leu Phe Ser Thr
370                 375                 380

Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
                 405                 410                 415

Gly Val Leu Gly Ala Gly Tyr Gln Ala Leu Arg Leu Ala Arg Ala Leu
             420                 425                 430

Leu Asp Gly Gln Glu Leu Met Phe Arg Gly Leu His Trp Val Met Glu
         435                 440                 445
```

-continued

Val Leu Gln Ala Thr Cys Arg Arg Thr Leu Glu Val Ala Arg Thr Ser
    450                 455                 460
Leu Leu Tyr Leu Ser Ser Ser Leu Gly Thr Glu Arg Phe Ser Ser Val
465                 470                 475                 480

Ala Gly Thr Pro Glu Ile Gln Glu Leu Lys Ala Ala Ala Glu Leu Arg
                485                 490                 495
Ser Arg Leu Arg Thr Leu Ala Glu Val Leu Ser Arg Cys Ser Gln Asn
            500                 505                 510
Ile Thr Glu Thr Gln Glu Ser Leu Ser Ser Leu Asn Arg Glu Leu Val
        515                 520                 525
Lys Ser Arg Asp Gln Val His Glu Asp Arg Ser Ile Gln Gln Ile Gln
    530                 535                 540
Cys Cys Leu Asp Lys Met Asn Phe Ile Tyr Lys Gln Phe Lys Lys Ser
545                 550                 555                 560
Arg Met Arg Pro Gly Leu Gly Tyr Asn Glu Glu Gln Ile His Lys Leu
                565                 570                 575
Asp Lys Val Asn Phe Ser His Leu Ala Lys Arg Leu Leu Gln Val Phe
            580                 585                 590
Gln Glu Glu Cys Val Gln Lys Tyr Gln Ala Ser Leu Val Thr His Gly
        595                 600                 605
Lys Arg Met Arg Val Val His Glu Thr Arg Asn His Leu Arg Leu Val
    610                 615                 620
Gly Cys Ser Val Ala Ala Cys Asn Thr Glu Ala Gln Gly Val Gln Glu
625                 630                 635                 640
Ser Leu Ser Lys Leu Leu Glu Glu Leu Ser His Gln Leu Leu Gln Asp
                645                 650                 655

Arg Ala Lys Gly Ala Gln Ala Ser Pro Pro Pro Ile Ala Pro Tyr Pro
            660                 665                 670
Ser Pro Thr Arg Lys Asp Leu Leu Leu His Met Gln Glu Leu Cys Glu
        675                 680                 685
Gly Met Lys Leu Leu Ala Ser Asp Leu Leu Asp Asn Asn Arg Ile Ile
    690                 695                 700
Glu Arg Leu Asn Arg Val Pro Ala Pro Pro Asp Val
705                 710                 715

<210> SEQ ID NO 44
<211> LENGTH: 716
<212> TYPE: PRT
<213> ORGANISM: Artificial Sequence
<220> FEATURE:
<223> OTHER INFORMATION: Description of Artificial Sequence: DT7-IKK3
      mutant

<400> SEQUENCE: 44

Met Gln Ser Thr Ala Asn Tyr Leu Trp His Thr Asp Asp Leu Leu Gly
  1               5                  10                  15

Gln Gly Ala Thr Ala Ser Val Tyr Lys Ala Arg Asn Lys Lys Ser Gly
             20                  25                  30

Glu Leu Val Ala Val Lys Val Phe Asn Thr Thr Ser Tyr Leu Arg Pro
         35                  40                  45

Arg Glu Val Gln Val Arg Glu Phe Glu Val Leu Arg Lys Leu Asn His
     50                  55                  60

Gln Asn Ile Val Lys Leu Phe Ala Val Glu Glu Thr Gly Gly Ser Arg
 65                  70                  75                  80

Gln Lys Val Leu Val Met Glu Tyr Cys Ser Ser Gly Ser Leu Leu Glu
                 85                  90                  95

-continued

Val Leu Glu Glu Pro Glu Asn Ala Phe Gly Leu Pro Glu Asp Glu Phe
        100                 105                 110

Leu Val Val Leu Arg Cys Val Ala Gly Met Asn His Leu Arg Glu
        115                 120                 125

Asn Gly Ile Val His Arg Asp Ile Lys Pro Gly Asn Ile Met Arg Leu
        130                 135                 140

Val Gly Glu Glu Gly Gln Ser Ile Tyr Lys Leu Thr Asp Phe Gly Ala
145                 150                 155                 160

Ala Arg Glu Leu Asp Asp Asp Glu Lys Phe Val Ser Val Tyr Gly Thr
                165                 170                 175

Glu Glu Tyr Leu His Pro Asp Met Tyr Glu Arg Ala Val Leu Arg Lys
            180                 185                 190

Pro Gln Lys Ala Phe Gly Val Thr Val Asp Leu Trp Ser Ile Gly
        195                 200                 205

Val Thr Leu Tyr His Ala Ala Thr Gly Ser Leu Pro Phe Ile Pro Phe
        210                 215                 220

Gly Gly Pro Arg Arg Asn Lys Glu Ile Met Tyr Arg Ile Thr Thr Glu
225                 230                 235                 240

Lys Pro Ala Gly Ala Ile Ala Gly Ala Gln Arg Arg Glu Asn Gly Pro
                245                 250                 255

Leu Glu Trp Ser Tyr Thr Leu Pro Ile Thr Cys Gln Leu Ser Leu Gly
            260                 265                 270

Leu Gln Ser Gln Leu Val Pro Ile Leu Ala Asn Ile Leu Glu Val Glu
        275                 280                 285

Gln Ala Lys Cys Trp Gly Phe Asp Gln Phe Phe Ala Glu Thr Ser Asp
        290                 295                 300

Ile Leu Gln Arg Val Val Val His Val Phe Ser Leu Ser Gln Ala Val
305                 310                 315                 320

Leu His His Ile Tyr Ile His Ala His Asn Thr Ile Ala Ile Phe Gln
                325                 330                 335

Glu Ala Val His Lys Gln Thr Ser Val Ala Pro Arg His Gln Glu Tyr
            340                 345                 350

Leu Phe Glu Gly His Leu Cys Val Leu Glu Pro Ser Val Ser Ala Gln
        355                 360                 365

His Ile Ala His Thr Thr Ala Ser Ser Pro Leu Thr Leu Phe Ser Thr
        370                 375                 380

Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
                405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
        435                 440                 445

Val Leu Gln Ala Thr Cys Arg Arg Thr Leu Glu Val Ala Arg Thr Ser
450                 455                 460

Leu Leu Tyr Leu Ser Ser Ser Leu Gly Thr Glu Arg Phe Ser Ser Val
465                 470                 475                 480

Ala Gly Thr Pro Glu Ile Gln Glu Leu Lys Ala Ala Glu Leu Arg
            485                 490                 495

Ser Arg Leu Arg Thr Leu Ala Glu Val Leu Ser Arg Cys Ser Gln Asn
        500                 505                 510

-continued

```
Ile Thr Glu Thr Gln Glu Ser Leu Ser Ser Leu Asn Arg Glu Leu Val
        515                 520                 525

Lys Ser Arg Asp Gln Val His Glu Asp Arg Ser Ile Gln Gln Ile Gln
    530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
                565                 570                 575

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
        595                 600                 605

Lys Arg Met Arg Val Val His Glu Thr Arg Asn His Leu Arg Leu Val
    610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
                645                 650                 655

Arg Ala Lys Gly Ala Gln Ala Ser Pro Pro Pro Ile Ala Pro Tyr Pro
            660                 665                 670

Ser Pro Thr Arg Lys Asp Leu Leu Leu His Met Gln Glu Leu Cys Glu
        675                 680                 685

Gly Met Lys Leu Leu Ala Ser Asp Leu Leu Asp Asn Asn Arg Ile Ile
    690                 695                 700

Glu Arg Leu Asn Arg Val Pro Ala Pro Pro Asp Val
705                 710                 715
```

<210> SEQ ID NO 45
<211> LENGTH: 716
<212> TYPE: PRT
<213> ORGANISM: Artificial Sequence
<220> FEATURE:
<223> OTHER INFORMATION: Description of Artificial Sequence: DT7-IKK3
mutant

<400> SEQUENCE: 45

```
Met Gln Ser Thr Ala Asn Tyr Leu Trp His Thr Asp Asp Leu Leu Gly
  1               5                  10                  15

Gln Gly Ala Thr Ala Ser Val Tyr Lys Ala Arg Asn Lys Lys Ser Gly
            20                  25                  30

Glu Leu Val Ala Val Lys Val Phe Asn Thr Thr Ser Tyr Leu Arg Pro
        35                  40                  45

Arg Glu Val Gln Val Arg Glu Phe Glu Val Leu Arg Lys Leu Asn His
    50                  55                  60

Gln Asn Ile Val Lys Leu Phe Ala Val Glu Glu Thr Gly Gly Ser Arg
 65                  70                  75                  80

Gln Lys Val Leu Val Met Glu Tyr Cys Ser Ser Gly Ser Leu Leu Ser
                85                  90                  95

Val Leu Glu Ser Pro Glu Asn Ala Phe Gly Leu Pro Glu Asp Glu Phe
            100                 105                 110

Leu Val Val Leu Arg Cys Val Val Ala Gly Met Asn His Leu Arg Glu
        115                 120                 125

Asn Gly Ile Val His Arg Asp Ile Lys Pro Gly Asn Ile Met Arg Leu
    130                 135                 140

Val Gly Glu Glu Gly Gln Ser Ile Tyr Lys Leu Thr Asp Phe Gly Ala
145                 150                 155                 160
```

-continued

```
Ala Arg Glu Leu Asp Asp Glu Lys Phe Val Glu Val Tyr Gly Thr
                165                 170                 175

Glu Glu Tyr Leu His Pro Asp Met Tyr Glu Arg Ala Val Leu Arg Lys
            180                 185                 190

Pro Gln Gln Lys Ala Phe Gly Val Thr Val Asp Leu Trp Ser Ile Gly
        195                 200                 205

Val Thr Leu Tyr His Ala Ala Thr Gly Ser Leu Pro Phe Ile Pro Phe
    210                 215                 220

Gly Gly Pro Arg Arg Asn Lys Glu Ile Met Tyr Arg Ile Thr Thr Glu
225                 230                 235                 240

Lys Pro Ala Gly Ala Ile Ala Gly Ala Gln Arg Arg Glu Asn Gly Pro
                245                 250                 255

Leu Glu Trp Ser Tyr Thr Leu Pro Ile Thr Cys Gln Leu Ser Leu Gly
            260                 265                 270

Leu Gln Ser Gln Leu Val Pro Ile Leu Ala Asn Ile Leu Glu Val Glu
        275                 280                 285

Gln Ala Lys Cys Trp Gly Phe Asp Gln Phe Phe Ala Glu Thr Ser Asp
    290                 295                 300

Ile Leu Gln Arg Val Val His Val Phe Ser Leu Ser Gln Ala Val
305                 310                 315                 320

Leu His His Ile Tyr Ile His Ala His Asn Thr Ile Ala Ile Phe Gln
                325                 330                 335

Glu Ala Val His Lys Gln Thr Ser Val Ala Pro Arg His Gln Glu Tyr
            340                 345                 350

Leu Phe Glu Gly His Leu Cys Val Leu Glu Pro Ser Val Ser Ala Gln
        355                 360                 365

His Ile Ala His Thr Thr Ala Ser Ser Pro Leu Thr Leu Phe Ser Thr
    370                 375                 380

Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
                405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
        435                 440                 445

Val Leu Gln Ala Thr Cys Arg Arg Thr Leu Glu Val Ala Arg Thr Ser
    450                 455                 460

Leu Leu Tyr Leu Ser Ser Ser Leu Gly Thr Glu Arg Phe Ser Ser Val
465                 470                 475                 480

Ala Gly Thr Pro Glu Ile Gln Glu Leu Lys Ala Ala Ala Glu Leu Arg
                485                 490                 495

Ser Arg Leu Arg Thr Leu Ala Glu Val Leu Ser Arg Cys Ser Gln Asn
            500                 505                 510

Ile Thr Glu Thr Gln Glu Ser Leu Ser Ser Leu Asn Arg Glu Leu Val
        515                 520                 525

Lys Ser Arg Asp Gln Val His Glu Asp Arg Ser Ile Gln Gln Ile Gln
    530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
                565                 570                 575
```

```
-continued

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
            595                 600                 605

Lys Arg Met Arg Val Val His Glu Thr Arg Asn His Leu Arg Leu Val
            610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
            645                 650                 655

Arg Ala Lys Gly Ala Gln Ala Ser Pro Pro Pro Ile Ala Pro Tyr Pro
            660                 665                 670

Ser Pro Thr Arg Lys Asp Leu Leu Leu His Met Gln Glu Leu Cys Glu
            675                 680                 685

Gly Met Lys Leu Leu Ala Ser Asp Leu Leu Asp Asn Asn Arg Ile Ile
            690                 695                 700

Glu Arg Leu Asn Arg Val Pro Ala Pro Pro Asp Val
705             710                 715
```

US 6,576,439 B1

IKK3 KINASE

This application is filed pursuant to 35 U.S.C. §371 as a U.S. National Phase Application of International Application No. PCT/JP99/07286 filed Dec. 24, 1999, which claims priority from GB 9828704.8 filed Dec. 24, 1998.

TECHNICAL FIELD

This invention relates to a novel IKK kinase protein, IKK3, nucleotides coding for it, vectors and host cells containing the same and methods for screening for modulators of said IKK3 protein for treatment of conditions involving inflammation.

BACKGROUND ART

The transcription factor NF-kB controls the activation of various genes in response to pathogens and pro-inflammatory cytokines. Thus, for example, NF-kB is activated by various kinds of stimulation including tumour necrosis factor alfa (TNF alfa) and interleukin-1 (IL-1), bacterial LPS, viral infection, antigen receptor cross-linking of T and B cells, calcium ionophores, phorbol esters, UV radiation and free radicals (for reviews, see Varma et al., 1995, Genes Dev., 9, 2723–2735; Baueurerle and Baltimore, 1996, Cell, 87, 13–20), (see FIG. 2). NF-kB in turn controls the activation of various genes in response to these stimuli. Activation of these various genes in turn may result in the production of cytokines, chemokines, leukocyte adhesion molecules, hematopoietic growth factors and may also effect development and cell death as well as cell survival (see FIG. 1). Specifically, the transcription factor NF-kB controls the activation of various genes in response to pathogens and pro-inflammatory cytokines. The NF-kB activity is regulated through interaction with specific inhibitors, IkBs. Upon cell stimulation, the IkBs are rapidly phosphorylated and then undergo ubiquitin-mediated proteolysis, resulting in the release of active NF-kB (Baldwin, 1996, Annu. Rev. Immunol., 14, 649–681; Baueurerle and Baltimore, 1996, Cell, 87, 13–20), (see FIG. 2). It has been reported that the 700 kDa complex specifically phosphorylated IkBα at S32 and S36 (Chen et al., 1996, Cell, 84, 853–862).

Several groups found. that two kinases termed IKK1 and IKK2 (also known as IKKα and IKKβ), were the subunits of the kinase complex. The groups showed that the IKKs immunoprecipitates, derived from the TNFα or IL-1 stimulated cells are able to phosphorylate IkB in vitro. In addition to these observations, two groups reported that IKK1 and IKK2 purified from insect cells are able to phosphorylate IkB in vitro. These results suggested that IKK directly phosphorylates IkBs. The over expression of anti-sense IKK1, kinase-inactive IKK1 or IKK2 resulted in the inhibition of NF-kB activation mediated by TNFα and IL-1. These results suggest that IKKs are critical kinases in the NF-kB activation pathway (May and Ghosh, 1998, Immunol. Today 19, 80–88; Stancovski and Baltimore, 1997, Cell, 91, 299–302). It has, however, not been understood how upstream signals are transmitted to the kinase complex, or whether different kinase complexes might exist to phosphorylate distinct IkBs.

NEMO (NF-kB essential modifier) and IKKγ (human homologue of the mouse NEMO) were isolated from purified IKK complex, and the inhibition of NEMO/IKKγ gene expression impaired the cytokine induced NF-kB activation via IKK1 and IKK2. In NEMO deficient cells, smaller complexes of Mr 3,000–4,000 are formed, though the normal complex is Mr 7,000–9,000, suggesting that NEMO/IKKγ physically link IkB kinase to upstream activators (Scheidereit, Nature, 1998, 395, 225–226).

The IKK-complex-associated protein (IKAP) was isolated from the IKK complexes. IKAP binds to IkB kinases and NIK and the complex, containing three kinases, leads to the maximum phosphorylation of IkB as compared to the complex containing one or two kinases. Accordingly, IKAP may act as scaffold proteins that link NIK or other molecules to IKK1 and IKK2 (Scheidereit, Nature, 1998, 395, 225–226). Accumulating evidence suggests that the IKK complex consists of several essential molecules, however, the molecular mechanisms that control the signalling complex were not well understood. Therefore, further association molecules were needed to complete the picture.

KIAA0151 was originally isolated from the KG-1 cDNA library (Nagase et al., 1995, DNA Res, 2, 167–174). KIAA0151 was identified as a potential Ser/Thr kinase, however, the importance of the molecule was not recognised. We have now found that KIAA0151 is similar to IKK1 and IKK2 using a computer homology analysis. KIAA0151, renamed IKK3, has a 21% homology with IKK1 and 23% with IKK2. IKK3 was able to phosphorylate IkB family proteins and directly phosphorylate IkB in vitro. The over expression of IKK3 leads to the activation of various inflammatory genes, such as IL-8, IL-6 and RANTES. These genes contain the NF-kB site in the gene regulation region. We know that IKK3 has an effect on IL-8 expression in Hela cells and also that IKK3 phosphorylates NF-kB. Moreover, it is known that the NF-kB site has an important role in IL-8 regulation. Our results suggest a correlation between IKK3 and the NF-kB site of the IL-8 promoter that has previously been identified as an endogenous NF-kB binding site, further suggesting that IKK3 plays an important role in controlling the NF-kB site of the IL-8 promoter. Specifically we have shown that IKK3 transactivates the IL-8 gene via the NF-kB binding to a site in the IL-8 promoter. These results lead to the conclusion that IKK3 is an important regulator of IL-8 gene regulation and thus activates genes that are important for the inflammatory diseases (see Table 1 below).

TABLE 1

Differences between IKK1, 2 and IKK3

|  | IKK1, 2 (also known as IKKα, β) | IKK3 |
| --- | --- | --- |
| Expression (mRNA) | Constitutive | Inducible by IL-1 and TNF-alfa |
| Source for in vitro phosphorylation | Mammalian and Insect cells | Mammalian and Bacterial cells |
| Spectrum | Unknown | IL-8, IL-6 and RANTES |
| Substrate Selectively | IkBα > IkBβ | IkBε IkBβ > IkBα |
| Enzymatic activity | Need for IL-1 or TNF alfa stimulation | No need for stimulation |

Using a computer homology analysis, we have now found that KIAA0151 is similar to IKK1 and IKK2. Importantly, recent experimental evidence has shown that IKK3 specifically controls various inflammatory genes, such as IL-8, IL-6 and RANTES. Moreover, IKK3 has been shown to phosphorylate various IkBs and directly phosphorylate TRIP9 (human IkBβ). IKK3 has therefore been shown to have a specific role in the control of inflammation.

DISCLOSURE OF INVENTION

Accordingly this invention provides a novel kinase protein, IKK3.

Nucleotide sequence analysis of IKK3 reveals a 2148 bp open reading frame which encodes 716 amino acid protein (FIG. 3). This deduced protein sequence shares many of the characteristics of IKK1 and IKK2. (see FIG. 5).

One aspect of the invention therefore provides an isolated IKK3 kinase protein or a variant thereof. The amino acid sequence of this isolated IKK3 kinase protein is shown in FIG. 3.

Included within the invention are variants of the IKK3 kinase protein. Such variants include fragments, analogues, derivatives and splice variants. The term "variant" refers to a protein or part of a protein which retains substantially the same biological function or activity as IKK3.

Fragments can include a part of IKK3 which retains sufficient identity of the original protein to be effective for example in a screen. Such fragments may be probes such as the ones described hereinafter for the identification of the full length protein. Fragments may be fused to other amino acids or proteins or may be comprised within a larger protein. Such a fragment may be comprised within a precursor protein designed for expression in a host. Therefore, in one aspect the term fragment means a portion or portions of a fusion protein or polypeptide derived from IKK3.

Fragments also include portions of IKK3 characterised by structural or functional attributes of the protein. These may have similar or improved chemical or biological activity or reduced side-effect activity. For example, fragments may comprise an alpha, alpha-helix or alpha-helix-forming region beta sheet and beta-sheet-forming region, turn and turn-forming regions, coil and coil-forming regions, hydrophilic regions, hydrophobic regions, amphipathic regions (alpha or beta), flexible regions, surface-forming regions, substrate binding regions and regions of high antigenic index.

Fragments or portions may be used for producing the corresponding full length protein by peptide synthesis.

Derivatives include naturally occurring allelic variants. An allelic variant is an alternate form of a protein sequence which may have a substitution, deletion or addition of one or more amino acids, which does not substantially alter the function of the protein. Derivatives can also be non-naturally occurring proteins or fragments in which a number of amino acids have been substituted, deleted or added. Proteins or fragments which have at least 70% identity to IKK3 are encompassed within the invention. Preferably, the identity is at least 80%, more preferably at least 90% and still more preferably at least or greater than 95% identity for example 97%, 98% or even 99% identity to IKK3.

Analogues include but are not limited to precusor proteins which can be activated by cleavage of the precursor portion to produce an active mature protein or a fusion with a compound such as polyethylene glycol or a leader/secretory to aid purification.

A splice variant is a protein product of the same gene, generated by alternative splicing of mRNA, that contains additions or deletions within the coding region (Lewin N (1995) Genes V Oxford University Press, Oxford, England). The present invention covers splice variants of the IKK3 kinase protein that occur naturally and which may play a role in the control of inflammation.

The protein or variant of the present invention may be a recombinant protein, a natural protein or a synthetic protein, preferably a recombinant protein.

A further aspect of the invention provides an isolated and/or purified nucleotide sequence which encodes a mammalian IKK3 protein as described above, or a variant thereof. Also included within the invention are anti-sense nucleotides or complementary strands.

Preferably, the nucleotide sequence encodes a rat or human IKK3 protein. The nucleotide sequence preferably comprises the sequence of the coding portion of the nucleotide sequence shown in FIG. 4.

A nucleotide sequence encoding an IKK3 protein of the present invention may be obtained from a cDNA or a genomic library derived from the human fetus Marathon-Ready cDNA (Clonetech).

The nucleotide sequence may be isolated from a mammalian cell (preferably a human cell), by screening with a probe derived from the rat, murine or human IKK3 sequence, or by other methodologies known in the art such as preliminary chain reaction (PCR) for example on genomic DNA with appropriate oligonucleotide primers derived from or designed based on rat or human IKK3 sequence and/or relatively conserved regions of known IKK3 proteins. A bacterial artificial chromosome library can be generated using rat or human DNA for the purposes of screening.

The nucleotide sequence of the present invention may be in form of RNA or in the form of DNA, which DNA includes cDNA, genomic DNA and synthetic DNA. The DNA may be double-stranded or single-stranded, and if single-stranded may be the coding strand or non-coding (anti-sense) strand. The coding sequence which encodes the IKK3 protein or variant thereof may be identical to the coding sequence set forth in FIG. 4, or maybe a different coding sequence which as a result of the redundancy or degeneracy of the genetic code, encodes the same protein as the sequences set forth therein.

A nucleotide sequence which encodes an IKK protein may include:

a coding sequence for the full length protein or any variant thereof;

a coding sequence for the full length protein or any variant thereof, and additional coding sequence such as a leader or secretory sequence or a pro-protein sequence: a coding sequence for the full length protein or any variant thereof (and optionally additional coding sequence) and non-coding sequences, such as intrans or non-coding sequences 5' and/or 3' of the coding sequence for the full length protein. The invention also provides nucleotide variants, analogues, derivatives and fragments which encode IKK3. Nucleotides are included which preferably have at least 70% identity over the entire length to IKK3. More preferred are those sequences which have at least 80% identity over their entire length to IKK3. Even more preferred are polynucleotides which demonstrate at least 90% for example 95%, 97%, 98% or 99% identity over their entire length to IKK3.

The present invention also relates to nucleotide probes constructed from the nucleotide sequence of an IKK protein or variant thereof. Such probes could be utilised to screen a cDNA or genomic library to isolate a nucleotide sequence encoding an IKK3 protein. The nucleotide probes can include portions of the nucleotide sequence of the IKK3 protein or variant thereof useful for hybridising with mRNA or DNA in assays to detect expression of the IKK3 protein or localised its presence on a chromosome using for example flourescence in situ hybridisation (FISH).

The nucleotide sequences of the invention may also have the coding sequence fused in frame to a marker sequence which allows for purification of the protein of the present invention such as hexa-histadine tag or hemagglutinin (HA) tag, Myc-tag, T7-tag, double MYC-tag, double HA-tag and double T7-tag expression vectors or allows determination in screening assays of effective blockage of IKK3 or it's modulation.

Nucleotide molecules which hybridise to IKK3 or to complementary nucleotides thereto also form part of the invention. Hybridisation is preferably under stringent hybridisation conditions. One example of stringent hybridisation conditions which is sometimes used is where attempted hybridisation is carried out at a temperature of from about 35° C. to about 65° C. using a salt solution which is about 0.9 mol. However, the skilled person will be able to vary such conditions as appropriate in order to take into account variables such as probe length, base composition, type of ions present etc. The nucleotide sequence of the present invention may be employed for producing the IKK3 protein or variant thereof by recombinant techniques. Thus, for example the nucleotide sequence may be included in any one of a variety of expression vehicles or cloning vehicles, in particular vectors or plasmids for expressing a protein, such vectors include chromosomal, non-chromosomal and synthetic DNA sequences. Examples of suitable vectors include derivatives of bacterial plasmids: phage DNA: yeast plasmids; vectors derived from combinations of plasmids and phage DNA and viral DNA. However, any other plasmid or vector may be used as long as it is replicable and viable in the host.

More particularly, the present invention also provides recombinant constructs comprising one or more of the nucleotide sequences as described above. The constructs comprise an expression vector, such as a plasmid or viral vector into which a sequence of the invention has been inserted, in a forward or reverse orientation. In a preferred aspect of this embodiment the construct further comprises one or more regulatory sequences to direct messenger mRNA synthesis, including, for example a promoter operably linked to the sequence. Suitable promoters include: CMV, LTR, or SV40 promoter and other promoters known to control expression of genes in prokaryotic or eukaryotic cells or their viruses. The expression vector may contain an enhancer and a ribosome binding site for translation initiation and transcription terminator.

Large numbers of suitable vectors and promoters/enhancers, will be known to those of skill in the art, but any plasmid or vector, promoter/enhancer may be used as long as it is replicable and functional in the host.

Appropriate cloning and expression vectors for use with prokaryotic and eurkaryotic hosts include mammalian expression vectors, insect expression vectors, yeast expression vectors, bacterial expression vectors and viral expression vectors and are described in Sambrook et al, Molecular Cloning: A Laboratory Manual, 2nd Edition, Cold Spring Harbor, N.Y., (1989). The vector may also include appropriate sequences for selection and/or amplification of expression. For this the vector will comprise one or more phenotypic selectable/amplifiable markers, such markers are also well known to those skilled in the art.

In a further embodiment, the present invention provides host cells capable of expressing a nucleotide sequence of the invention, the host cell can be, for example, a higher eukaryotic cell, such as mammalian cell or a lower eukaryotic cell, such as a yeast cell or a prokaryotic cell such as a bacterial cell. Suitable prokaryotic hosts for transformation include E-coli. Other examples include viral expression vectors, insect expression systems and yeast expression systems.

Cell-free translation systems can also be employed to produce such proteins using RNAs derived from the DNA constructs of the present invention.

The IKK3. protein is recovered and purified from recombinant cell cultures by methods known in the art, including ammonium sulfate or ethanol precipitation, acid extraction, and ion or cation exchange chromatography, phosphocellulose chromatography and lecitin chromatography. Protein refolding steps may be used, as necessary, in completing configuration of the mature protein. Finally high performance liquid chromatography (HPLC) can be employed for final purification steps.

The proteins and nucleotide sequences of the present invention are preferably provided in an isolated form. The term "isolated" means that the material is removed from its original environment e.g. the naturally-occurring nucleotide sequence or protein present in a living animal is not isolated, but the same nucleotide sequence or protein, separated from some or all of the materials it co-exists within the natural system, is isolated. Such nucleotide sequence could be part of a vector and/or such nucleotide sequence or protein could be part of a composition, and still be isolated in that such vector or composition is not part of its natural environment. The proteins and nucleotide sequences of the present invention are also preferably provided in purified form, and preferably are purified to at least 50% purity, more preferably about 75% purity, most preferably 90% purity or greater such as 95%, 98% pure.

The present invention also provides antibodies specific for the IKK3 protein. The term antibody as used herein includes all immunoglobulins and fragments thereof which contain recognition sites for antigenic determinants of proteins of the present invention. The antibodies of the present invention may be polyclonal or preferably monoclonal, may be intact antibody molecules or fragments containing the active binding region of the antibody, e.g. Fab or (Fab)$_2$. The present invention also includes chimaeric, single chain and humanised antibodies and fusions with non-immunoglobulin molecules. Various procedures known in the art may be used for the production of such antibodies and fragments.

The proteins, their variants especially fragments, derivatives, or analogues thereof, or cells expressing them can be used as an immunogen to produce antibodies thereto. Antibodies generated against the IKK3 protein can be obtained by direct injection of the polypeptide into an animal, preferably a non-human. The antibody so obtained will then bind the protein itself. In this manner, even a sequence encoding only a fragment of the protein can then be used to generate antibodies binding the whole native protein. Such antibodies can be used to locate the protein in tissue expressing that protein.

The antibodies of the present invention may also be of interest in purifying an IKK3 protein and accordingly there is provided a method of purifying an IKK3 protein or any portion thereof which method comprises the use of an antibody of the present invention.

The present invention also provides methods of identifying modulators of the IKK3 protein. Screens can be established for IKK3 enabling large numbers of compounds to be studied. High throughput screens may be based on $_{14}$C guanidine flux assays and flourescence based assays as described in more detail below. Secondary screens may involve electrophysiological assays utilising patch clamp technology or two electrode voltage clamps to identify small molecules, antibodies, peptides, proteins or other types of compounds that inhibit, block, or otherwise interact with the IKK3 protein. Tertiary screens may involve the study of the modulators in well characterised rat and mouse models of inflammation. These models of inflammation include, but are not restricted to inflammatory models (murine) atopic dermatitis models (murine and rat), repeated-induced type dermatitis model (murine) and allergic asthma models (murine and guinea pig). For example, screens may be set up based on an in vitro phosphorylation system using bacterially expressd IKK3 proteins (see Example 5 and FIG. 12). This system may be used to screen for modulators of the IKK3 kinase activity and then subsequently testing the effect of potential modulators of IKK3 on gene expression, specifically the expression of IL-8, IL-6 and RANTES using cell based assay systems. Finally the efficacy of these modulators in relation to inflammatory or allergic diseases may be tested on models of inflammation.

The invention therefore provides a method of assaying for a modulator comprising contacting a test compound with the IKK3 protein and detecting the activity or inactivity of the IKK3 protein. Preferably, the methods of identifying modulators or screening assays employed transformed host cells that express the IKK3 protein. Typically, such assays will detect changes in the activity of the IKK3 protein to the test compound, thus identifying modulators of the IKK3 protein.

In general, a test compound is added to the assay and its effect on IKK3 is determined or the test compound's ability to competitively bind to the IKK3 is assessed. Test compounds having the desired effect on the IKK3 protein are then selected.

IL-8, IL-6 and RANTES are involved in diseases involving inflammation and allergies. Specifically, asthma, atopic dermatitis, arthritis, rheumatoid arthritis, systemic lupus erythematosus, LPS—induced contact dermatitis, glomerulonephritis, gout and other inflammation-related diseases.

The invention therefore provides a modulator of a protein or a variant thereof as described above identifiable by a method described above for use in therapy. The invention further provides use of a modulator of an IKK3 protein optionally identifiable by a method described above for the manufacture of an anti-inflammatory medicament. Moreover the invention provides a method of treatment which comprises administering to a patient an effective amount of a modulator of a protein as described above. More specifically, the invention provides a method of treating diseases related to inflammation, such as asthma, atopic dermatitis, arthritis, rheumatoid arthritis, systemic lupus erythematosus, LPS—induced contact dermatitis, glomerulonephritis and gout.

Complementary or anti-sense strands of the nucleotide sequences as herein above defined can be used in gene therapy. For example, the cDNA sequence of fragments thereof could be used in gene therapy strategies to down regulate the IKK3 protein. Anti-sense technology can be used to control gene expression through triple-helix formation of anti-sense DNA or RNA, both of which methods are based on binding of a nucleotide sequence to DNA or RNA.

A DNA oligonucleotide is designed to be complementary to a region of the gene involved in transcription thereby preventing transcription and the product of the sodium channel. The anti-sense RNA oligonucleotide hybridises to the messenger RNA in vivo and blocks translation of the messenger RNA into the IKK3 protein.

The regulatory regions controlling expression of the IKK3 protein could be used in gene therapy to control expression of a therapeutic construct in cells expressing the IKK3 protein.

Outside factors stimulating expression of NF-kB as well as the effect of NF-kB on various biological events.

FIG. 2

Regulation of NF-kB activity.

FIG. 3

Predicted amino acid sequence of IKK3:
 The potential kinase domain (KD) and helix-loop-helix (HLH) are boxed. The potential leucine zipper is underlined. Asterisk and dots indicate identical and similar amino acids, respectively. Numbers in the right hand column indicate position of the amino acids.

FIG. 4

Nucleotide sequence of IKK3:
 Numbers in left hand column indicate position of nucleic acid.

FIG. 5

Schematic representation of IKK alpha, beta and IKK3 (KD=kinase domain; LZ=leucine zipper, HLH=helix-loop-helix). IKK3 is 21% identical to IKK1 and 23% identical to IKK2 at the amino acid level. IKK1 has a 52% identity to IKK2 at the amino acid level.

FIG. 6

Northern blot analysis:
 Inducile expression of IKK3.

FIG. 7

A. In vitro phosphorylation of IkB proteins by IKK3.

B. In vitro phosphorylation of IkB mutant proteins by IKK3.

FIG. 8

In vitro phosphorylation of TRIP9 by IKK3 mutants.
 A. Schematic representation of IKK3 mutant proteins.
 B. IKK3 mutant proteins were separated by SDS-PAGE, stained with Coomassie blue and analyzed by autoradiography.

FIG. 9

IKK3 directly phosphorylates TRIP9.

FIG. 10

IKK3 mediates the expression of various chemokines and cytokines

FIG. 11

IKK3 mediates the expression of IL-8 RNA.

Figure 12:
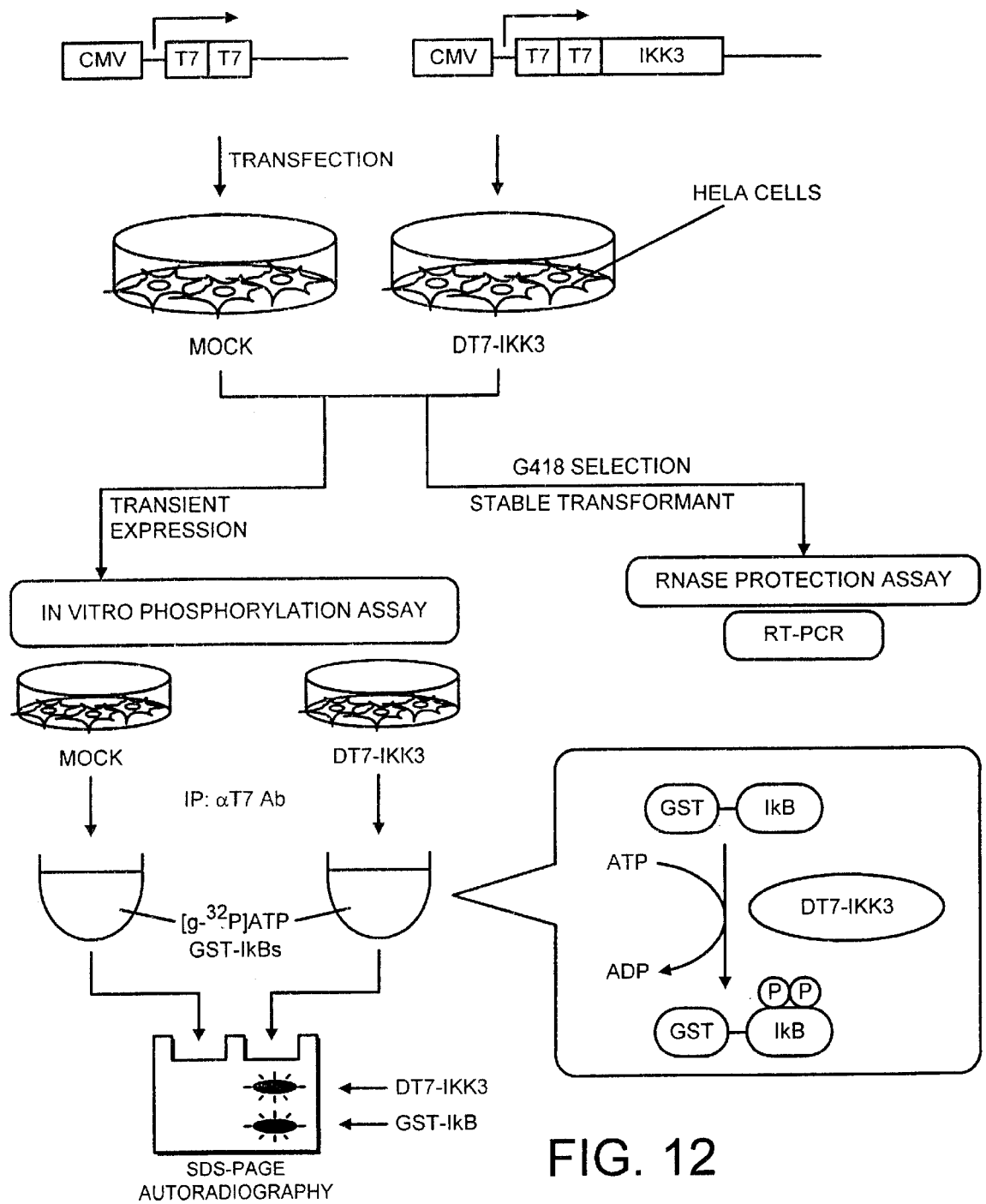

FIG. 12 A brief outline of an in vitro phosphorylation assay (IkB)

The double T7-tagged IKK3 expression vector (DT7-IKK3) or the double T7-tagged control vector (Mock) is transfected into Hela cells. The cell lysates are used for the in vitro phosphorylation assay. The tagged proteins are immunoprecipitated with anti-T7 antibody (Novogen), mixed with GST-IkBs and [γ-32]ATP. The mixtures are separated by SDS-PAGE and analyzed by autoradiography. The immunoprecipitate of DT7-IKK3 is able to phosphorylate IkBs.

Figure 13:
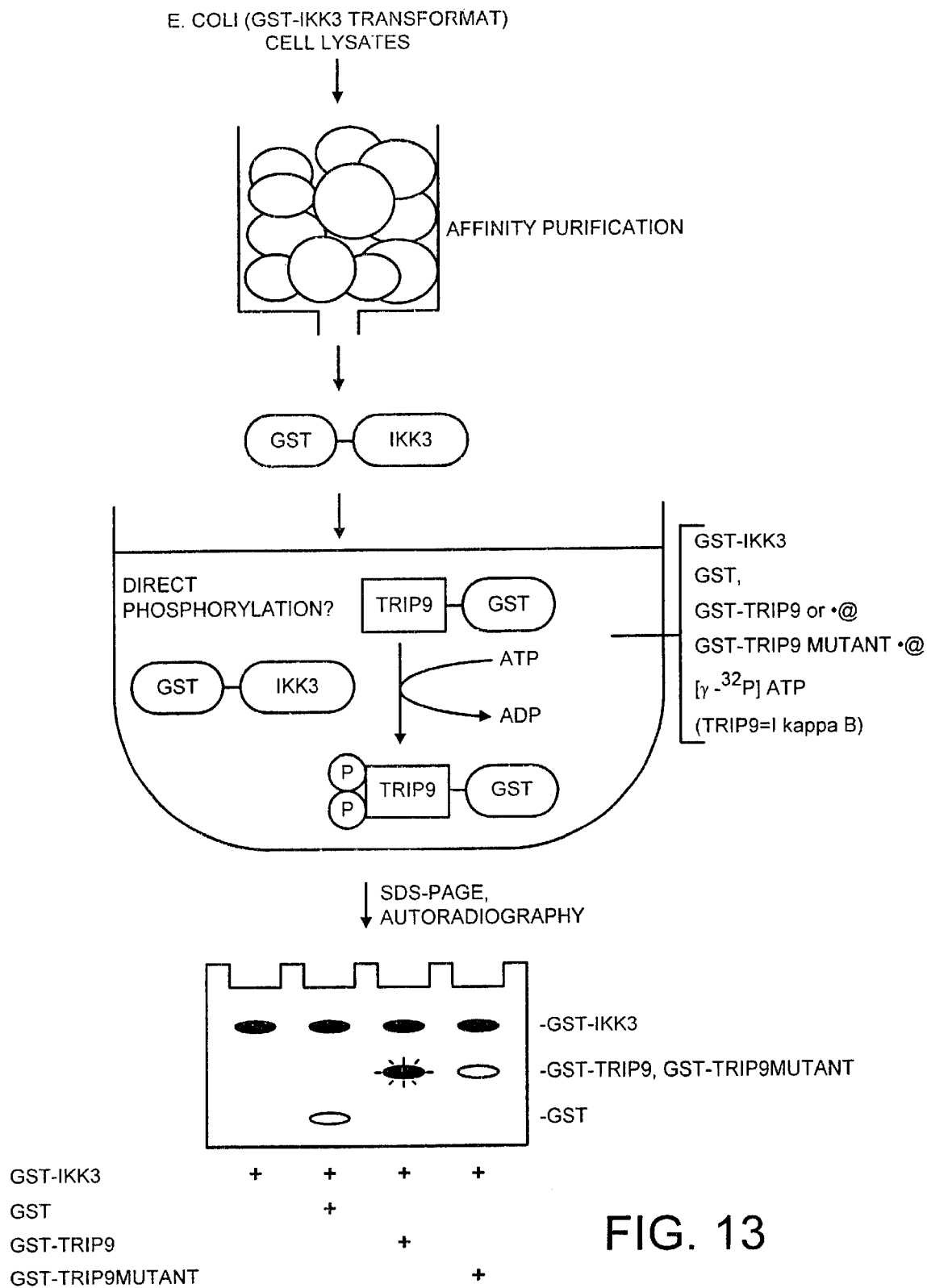

FIG. 13 A brief outline of an in vitro phosphorylation assay (TRIP9)

The GST-IKK3 protein was expressed in *E. Coli*, and the protein was affinity purified by the GST column, and used for the in vitro phosphorylation assay. The GST-IKK3 was incubated with [γ-32]ATP and GST, GST- IkBβ (TRIP9) or GST-IkBβ or GST-IkBβ (TRIP9) mutant. The protein mixture was separated by SDS-PAGE and analyzed by autoradiography. Result shows that the GST-IKK3 directly phosphorylates GST-IkBβ (TRIP9), but not GST and GST-IkBβ mutant.

Figure 14:
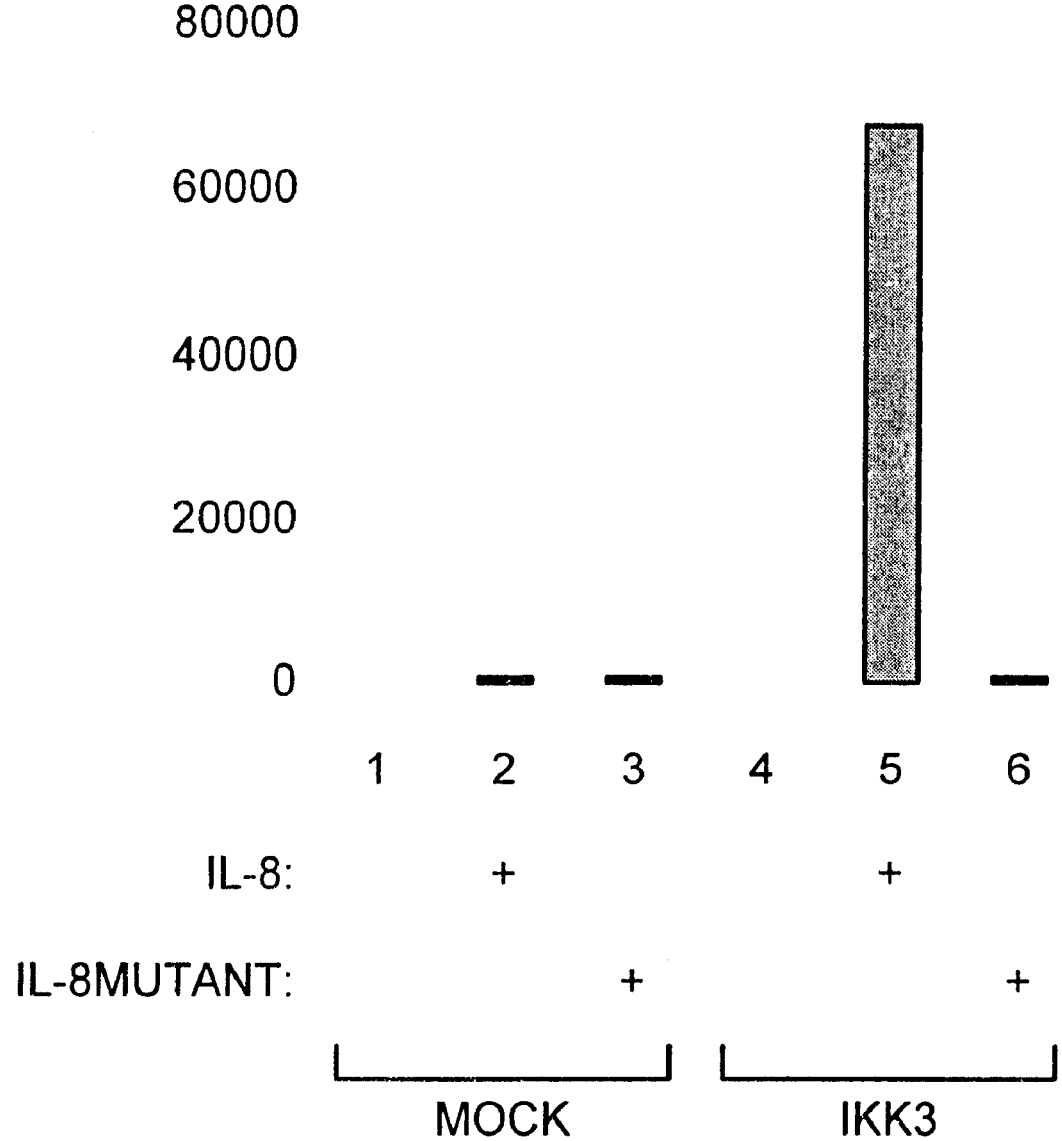

FIG. 14 IKK3 regulates the NF-κB site of IL-8

IKK3 controls an essential step in the NF-kB signalling pathway. Hela cells were transiently transfected with the IL-8 or the IL-8 mutant luciferase reporter gene plasmid, and the expression vector encoding double T7-tagged IKK3 (IKK3), or with a vector control (Mock). Luciferase activities were determined and normalized on the basis of β-galactosidase expression from cotransfected pact-β-Gal.

Figure 15:
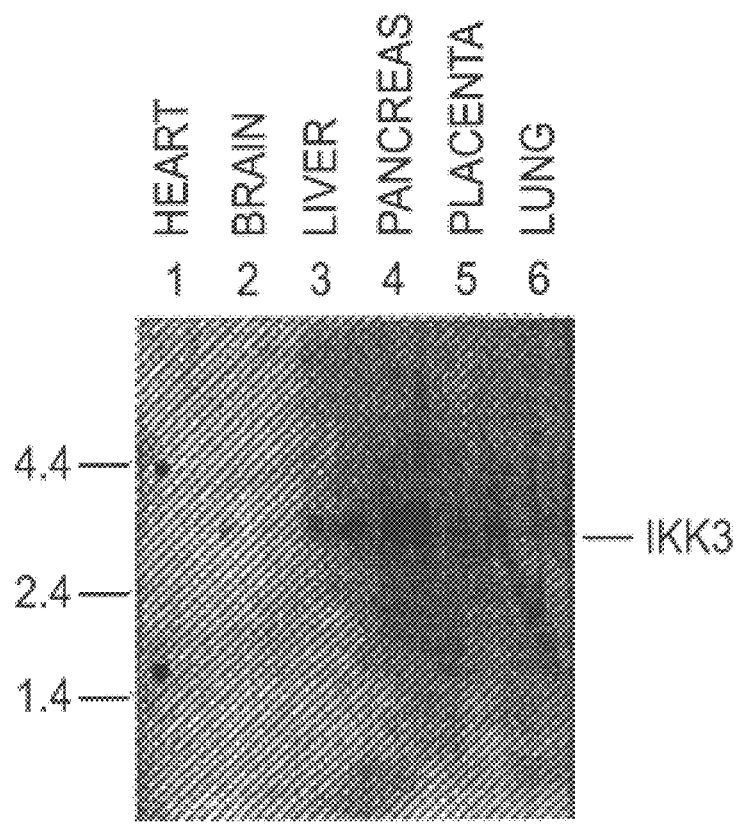

FIG. 15 Northern blot analysis

The human tissue filter for the northern blot (gene hunter, TOYOBO) was probed with the IKK3 specific primers.

FIG. 16 Antibody against IKK3 effect on the kinase activity of IKK3.

A. The bacterially expressed GST-IKK3 were incubated with the bacterially expressed GST-TRIP9 (IkBβ), -TRIP9/AA, antibody and [γ-$^{32}$P]ATP for 30 min at 30° C. Proteins were separated by SDS-PAGE, stained with Coomassie blue and analyzed by autoradiography.

B. IKK3 antibody activate the IKK3 kinase acitivity. The amount of GST-TRIP9 phosphoprotein was counted by Image analyzer (Fuji Film).

BEST MODE FOR CARRYING OUT THE INVENTION

EXAMPLE 1

Materials and Methods

Cells and Transfection

Hela cells were maintained in Dulbecco's modified Eagle's medium (DMEM) with 10% fetal calf serum. DNA transfection into cells was done by DOSPER transfection according to the manufacture's instructions.

Vector Construction

IKK1, IKK2, IKK3, IkBα, IkBβ, TRIP9, IkBε cDNAs were obtained by PCR from the human fetus Marathon-Ready cDNA (Clonetech). The primers were as follows:

IKK1 (Accession number AF012890; nucleotides 1–2238; 5'primer G87, 3' primer G88)

IKK2 (Accession number AF029684; nucleotides 1–2268; 5'primer G89, 3' primer G90)

IKK3 (Accession number D63485; nucleotides 327–2477; 5'primer G85, 3' primer G90)

IkBα (Accession number, M69043; nucleotides 95–256, 5'primer G91, 3'primer G138)

IkBβ (Accession number, I34460; nucleotides 74–205, 5'primer G93, 3'primer G147)

TRIP9 (Accession number, L40407; nucleotides 53–184, 5'primer G97, 3'primer G148)

IkBε (Accession number, U91616; nucleotides 451–765, 5'primer G150, 3'primer G149)

The cDNA fragment was digested with NotI and the fragment was subcloned into DT7-CMV (Takemoto et al, 1997, DNA and Cell Biol., 16, 893–896).

Site-directed Mutagenesis

Site-directed mutagenesis was performed with QuikChange™ site-directed mutagenesis kit (STRATAGENE) according to the manufacture's instructions.

TABLE 2

Primers used

| | |
|---|---|
| G7-5 | 5'-TCCTGATTTCTGCAGCTCTG-3' |
| G7-3 | 5'-AACTTCTCCACAACCCTCTG-3' |
| G85 | 5'-CCCCCCGCGGCCGCCACCATGCAGAGCACAGCCAATTACCTGTGG-3' |
| G86 | 5'-CCCCCCGCGGCCGCCTCAGACATCAGGAGGTGCTGGGACTCTATT-3' |
| G87 | 5'-CCCCCCGCGGCCGCCATGGAGCGGCCCCGGGGCTGCGGCCGGGC-3' |
| G88 | 5'-CCCCCCGCGGCCGCCTCATTCTGTTAACCAACTCCAATCAAGATT-3' |
| G89 | 5'-CCCCCCGCGGCCGCCATGAGCTGGTCACCTTCCCTGACAACGCAG-3' |
| G90 | 5'-CCCCCCGCGGCCGCCTCATGAGGCCTGCTCCAGGCAGCTGTGCTC-3' |
| G91 | 5'-CCCCCCGCGGCCGCCATGTTCCAGGCGGCCGAGCGCCCCCAGGAG-3' |
| G138 | 5'-CCCCCCGCGGCCGCCTCAGAGGCGGATCTCCTGCAGCTCCTTGAC-3' |
| G93 | 5'-CCCCCCGCGGCCGCCATGGCCGGGGTCGCGTGCTTGGGGAAAACT-3' |
| G147 | 5'-CCCCCCGCGGCCGCCTCACAGCTCTGGGCCAAGCTCTGCGCCCAG-3' |
| G97 | 5'-CCCCCCGCGGCCGCCATGGCTGGGGTCGCGTGCTTGGGAAAAGCT-3' |
| G148 | 5'-CCCCCCGCGGCCGCCTCACAGCCCCGGGCCCAACTCCGCGCCCAA-3' |
| G150 | '5-CCCCCCGCGGCCGCATGTCGGAGGCGCGGAAGGGGCCGGACGAG-3' |
| G149 | '5-CCCCCCGCGGCCGCCTCACAGCGCCCCCACGTGGGGGAGTGGCAG-3' |
| G124 | 5'-GAGCTGGTTGCTGTGATGGTCTTCAACACTACC-3' |
| G125 | 5'-GGTAGTGTTGAAGACCATCACAGCAACCAGCTC-3' |
| G126 | 5'-AGTGGGAGCCTGCTGGCTGTRGCTGGAGGCTCCTGAGAATGCCTTT-3' |
| G127 | 5'-AAAGCATTCTCAGGAGCCTCCAGCACAGCCAGCAGGCTCCCACT-3' |
| G130 | 5'-GAGCTGGATGATGATGCGAAGTTCGTCGCGGTCTATGGGACTGAG-3' |
| G131 | 5'-CTCAGTCCCATAGACCGCGACGAACTTCGATCATCATCCAGCTC-3' |
| G128 | 5'-AGTGGGAGCCTGCTGGAGGTGCTGGAGGAGCCTGAGAATGCCTTT-3' |
| G129 | 5'-AAAGGCATTCTCAGGCTCCTCCAGCACCTCCAGCAGGCTCCCACT-3' |
| G132 | 5'-GATGAGAAGTTCGTCGAGGTCTATGGGACTGAG-3' |
| G133 | 5'-CTCAGTCCCATAGACCTCGACGAACTTCTCATC-3' |
| G136 | 5'-GACGACCGCCACGACGCCGGCCTGGACGCCATGAAAGACGAGGAG-3' |
| G137 | 5'-CTCCTCGTCTTTCATGGCGTCCAGGCCGGCGTCGTGGCGGTCGTC-3' |
| G178 | 5'-GATGAATGGTGCGACGCCGGCCTGGGCGCTCTAGGTCCCGACGCA-3' |
| G171 | 5'-TGCGTCGGGACCTAGAGCGCCCAGGCCGGCGTCGCACCATTCATC-3' |
| G172 | 5'-GATGAATGGTGCGACGCCGCCTGGGCGCCCTGGGTCCGGACGCA-3' |
| G173 | 5'-TGCGTCCGGACCCAGGGCGCCCAGGCCGGCGTCGCACCATTCATC-3' |
| G174 | 5'-GAGAGCCAGTACCACGCTGGCATTGAGGCTCTGCGCTCTCTGCGC-3' |
| G175 | 5'-GCGCAGAGAGCGCAGAGCCTCAATGCCAGCGTCGTACTGGCTCTC-3' |
| G176 | 5'-GGGGAGCGGGCTGATGCCACCTATGCGCCTCCTCGCTCACCTAC-3' |
| G177 | 5'-GTAGGTGAGCGAGGAGGCGCCCATAGGTGGCATCAGCCCGCTCCCC-3' |

DT7-IKK3 mutants:
  Met38 of DT7-IKK3 was mutated to Ala (DT7-DN1 DT7-DN1, nucleotides 432–455; 5' primer G124 and 3' primer G125);
  Ser96 and Ser100 of DT7-IKK3 were mutated to Ala (DT7-DN2, nucleotides 597–641; 5' primer G126 and 3' primer G127);
  Ser 168 and Ser 172 of DT7-IKK3 were mutated to Ala (DT7-DN3, nucleotides 813–857; 5' primer G130 and 3' primer G131);
  Ser96 and Ser100 of DT7-IKK3 were mutated to Glu (DT7-EE1, nucleotides 597–641; 5' primer G128 and 3' primer G129);
  Ser 172 of DT7-IKK3 was mutated to Glu (DT7-EE2, nucleotides 813–857; 5' primer G132 and 3' primer G133).

GST-IkB Mutants:
  Ser32 and Ser36 of GST-IkBα were mutated to Ala (GST-IkBα/AA: nucleotides 173–217; 5' primer G136 and 3' primer G137);
  Ser19 and Ser23 of GST-IkBβ were mutated to Ala (GST-IkBβ/AA: nucleotides 113–157; 5'primer G178 and 3' primer G171);
  Ser19 and Ser23 of GST-TRIP9 were mutated to Ala (GST-TRIP9/AA: nucleotides 92–136; 5' primer G172 and 3' primer G173);
  Ser157 and Ser161 of GST-IkB ε were mutated to Ala (GST-IkB ε/AA1: nucleotides 487–531; 5' primer G174 and 3' primer G175);
  Ser210 and Ser214 of GST-IkB ε were mutated to Ala (GST-IkB ε/AA2: nucleotides 646–690; 5' primer G176 and 3' primer G177).

All PCR-derived sequences used in this study were confirmed by the Sangar method.

EXAMPLE 2
Northern Blot Analysis: Inducible Expression of IKK3

Cells were treated with IL-1α (10 ng/ml), TNF-α (100 ng/ml), IFN-γ (10 ng/ml), LPS (100 ng/ml) or C2-ceramide (50 μM) for 5 hours, and the total RNAs were analyzed by Northern blot analysis with the IKK3 specific primers. The expression of actin RNA was used as a control. It was found that IKK3 gene expression was induced by 1L-1 or TNFα stimulation in human Hela cells (see FIG. 6).

EXAMPLE 3
Rnase Protection Assay

Hela cells were stably expressed with double T7-tagged IKK3. The cells were treated with IL-1α (10 ng/ml) or TNF-α (100 ng/ml). Total RNA was isolated by ISOGEN (Nippongene) according to the manufacture's instructions and subjected to Rnase protection assay. The bands of each genes were normalized by the G3PDH expression.

EXAMPLE 4
RT-PCR cDNA was prepared from 5 μg of total RNA using M-MTLV reverse transcriptase (Life Technologies) to a final volume of 100 μl . After a 90-min incubation of the mixture at 37, the cDNA solution was ethanol-precipitated and resuspended in 100 μl of water. The cDNA was amplified by PCR with the IL-8 specific primers (5' primer G7-5 and 3' primer G7-3; Accession number, M28130; nucleotides, 1621 bp and 2945 bp of the genomic DNA) and the G3PDH specific primers (Clonetech). Expected PCR products (238 bp for IL-8 and 983 bp for G3PDH) were size-fractionated onto a 1.8% agarose gel and stained with ethidium bromide.

Figure 7A:
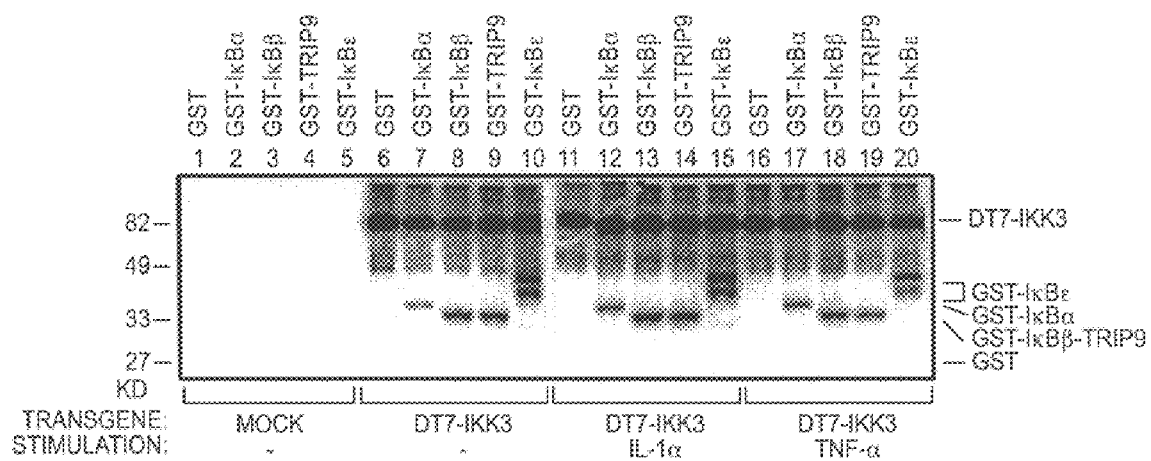
Figure 7B:
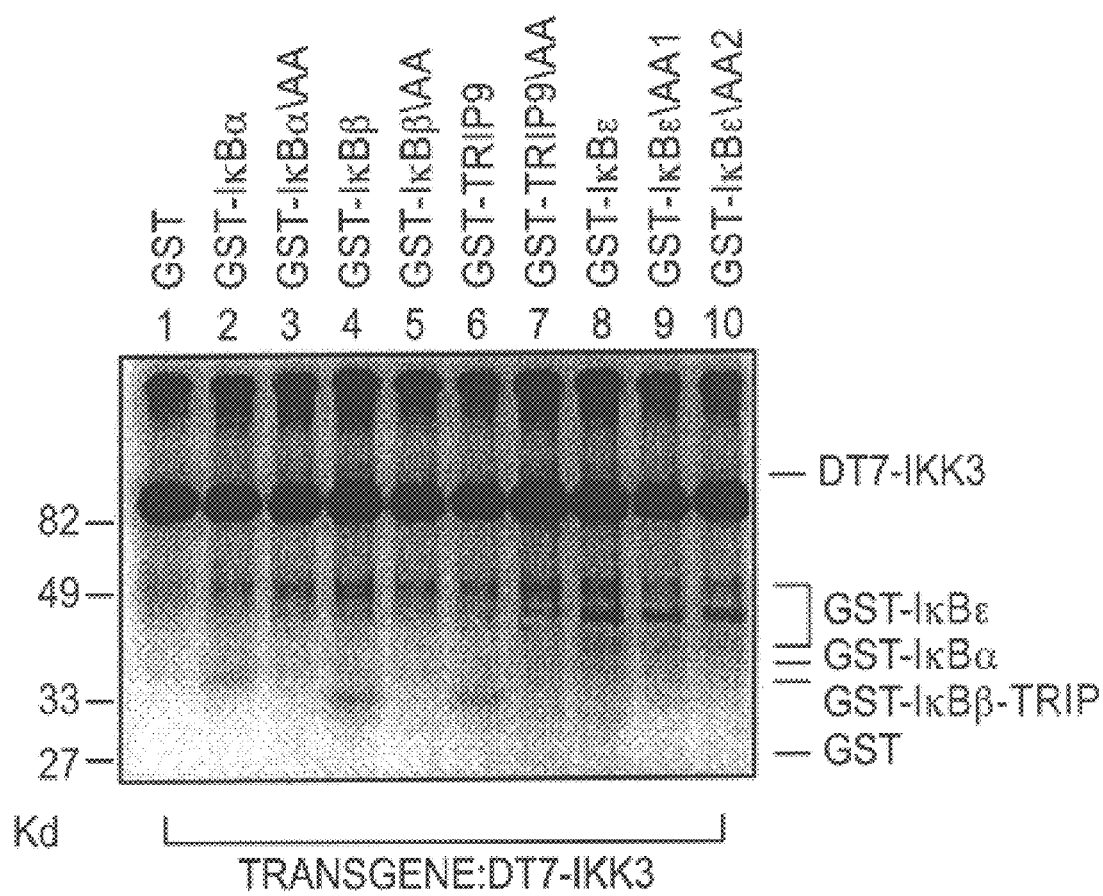

EXAMPLE 5
In vitro Phosphorylation of IkB Proteins by IKK3: Target Molecules of IKK3 and IKK3 Activation Hela cells were transiently expressed with the double T7-tagged IKK3 expression vector. (DT7-IKK3) or the double T7-tagged control vector (Mock) is transfected into Hela cells. Thirty-six hours after transfection, the cells were treated with IL-1α (10 ng/ml) or TNF-α (100 ng/ml) for 10 min. Cells were prepared by lysis with TNE buffer (10 mM Tris-HCl, pH 7.8; 1% NP-40, 0.15 M. NaCl; 1 mM EDTA; 10 nM NaF, 2 mM Na3V04, 10 mM PNPP and complete) and IKK3 proteins were immunoprecipitated with anti-T7 antibody (Novogen). Purified DT-IKK3 were used for in vitro kinase reactions with bacterially expressed GST, GST-IkBα (1–54), -IkBβ (1–44), -IkBε (140–244), -TRIP9 (1–44) and [γ-$^{32}$P] ATP. The alanine-substitution mutants GST IkBα (IkBα/AA), -IkBβ (IkBβ/AA), -TRIP9 (1–44, AA), -IkBε (IkBε/AA1 and IkBε/AA2) were used as control proteins. Proteins were separated by SDS-PAGE, stained with Coomassie blue analyzed by autoradiography (see FIG. 7). It was found that IKK3 phosphorylates I kappa B (IkB) α, IkB β and IkBε. IKK3 phosphorylates IkB ε and IkB β in preference to IkB α. When IKK3 is over expressed in Hela cells, no stimulation was needed to activate IKK3 (see FIG. 7a—no stimulation, lanes 6–10; IL-1 stimulation, lanes 11–15; TNF alpha stimulation, lanes 16–20). IKK3 is able to phosphorylate IkBs with or without stimulation, such as IL-1 and TNF-alpha. For a brief outline of the experiment see FIG. 12. IKK3 is unable to phosphorylate IkB α/AA, IkB β/AA and TRIP9/AA (see FIG. 7b).

EXAMPLE 6
In vitro Phosphorylation of TRIP9 by IKK3 Mutants

Met38 of DT7-IKK3 was mutated to Ala (DN1); Ser96 and Ser100 of DT7-IKK3 were mutated to Ala (DN2); Ser 168 and Ser 172 of DT7-IKK3 were mutated to Ala (DN3); Ser96 and Ser100 of DT7-IKK3 were mutated to Glu (EE1); Ser172 of DT7-IKK3 was mutated to Glu (EE2).

Figure 8A:
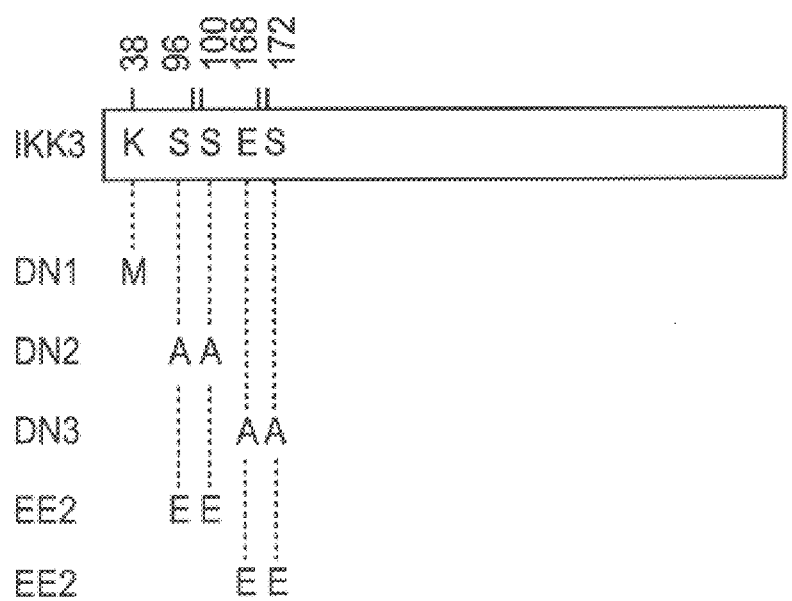
Figure 8B:
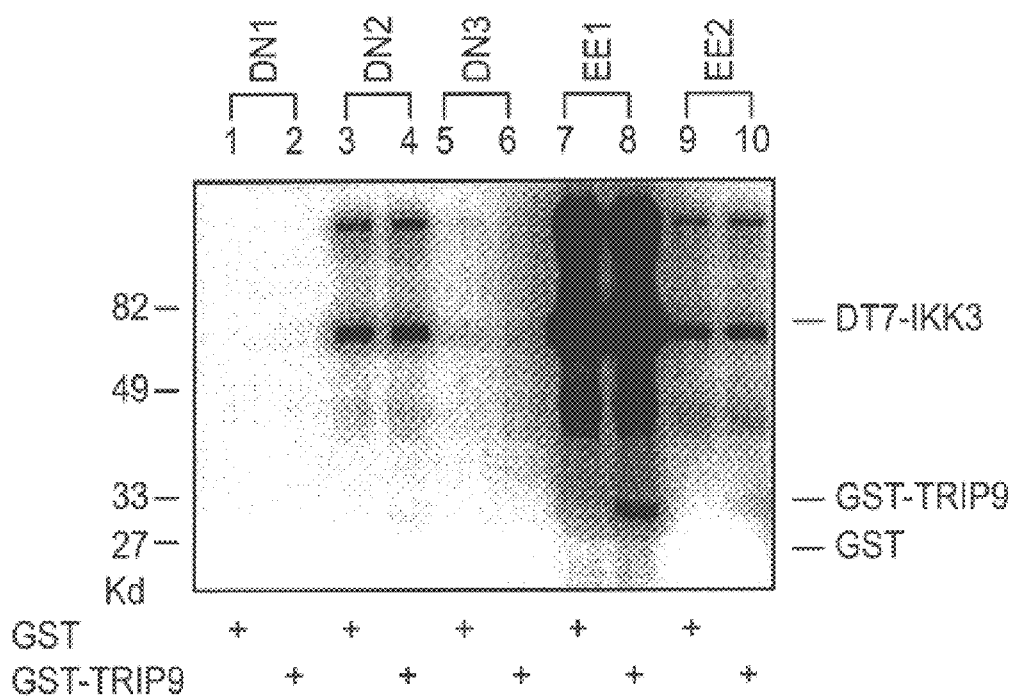

Hela cells were transiently expressed with the double T7-tagged IKK3 mutant expression vectors. Thirty-six hours after tranfection, IKK3 mutant proteins were immunoprecipitated with anti-T7 antibody. Purified DT-IKK3 mutants were used for in vitro kinase reactions with bacterially expressed GST, GST-TRIP9 (1–44) and [γ-$^{32}$P] ATP. GST were used as control proteins. Proteins were separated by SDS-PAGE, stained with Coomassie blue and analyzed by autoradiography (see FIG. 8). It was found that some amino acids play an important role in the IKK3 kinase activity (FIG. 8). We found some mutation of IKK3 reduced the kinase activity of the mutants (DN1, DN2 and DN3 (FIG. 8b, lanes 1–6). The EE1 mutation strongly enhances the kinase activity of EE1 (FIG. 8b, lanes 7 and 8). The mutant of EE2 has only a small effect on the kinase activity of EE2 (FIG. 8b, lanes 9 and 10). The immunoprecipitate of DT7-IKK3 is able to phosphorylate IkBabeta (TRIP9). The brief outline of the experiment is shown in FIG. 12.

EXAMPLE 7
In vitro Phosphorylation: IKK3 Directly Phosphorylates TRIP9

The bacterially expressed GST-IKK3 were incubated with the bacterially expressed GST, GST-TRIP9 (1–44), -TRIP (1–44, AA) and [γ-$^{32}$P] ATP for 30 min at 30° C.

Figure 9:
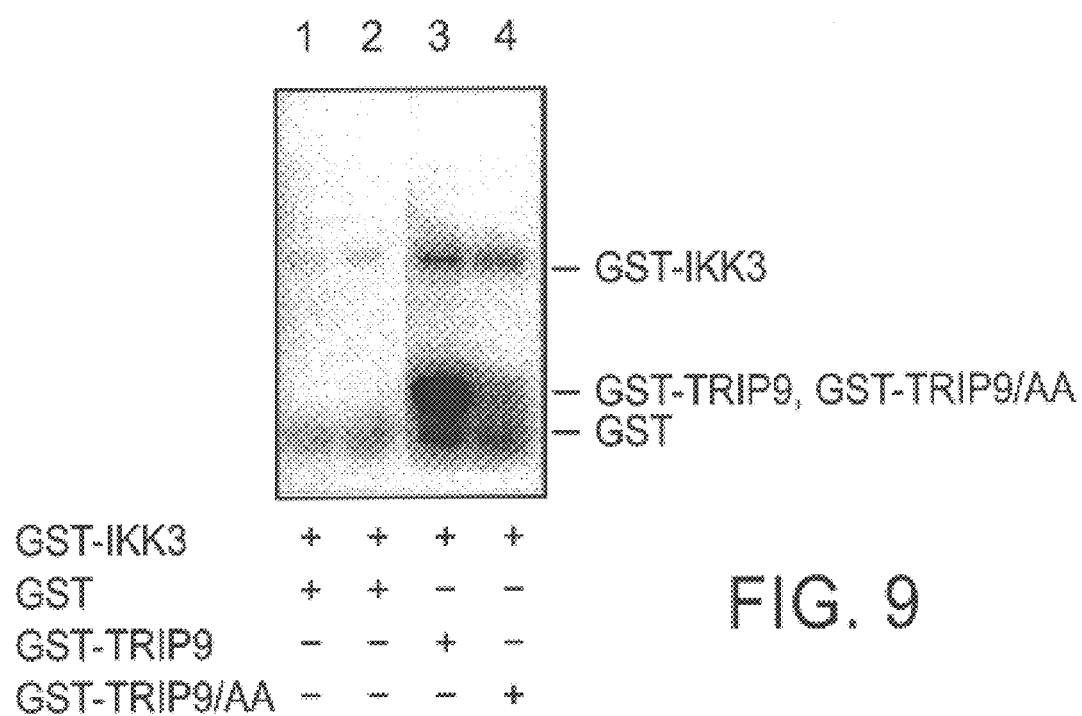

The bacterially expressed GST-DT-IKK3 was used as a kinase. A 250 ng of purified kinase solution was used for in vitro kinase reactions with a 500 ng of bacterially expressed GST, GST-TRIP9 (1–44), -TRIP (1–44, AA) and [γ-$^{32}$P] ATP. Proteins were separated by SDS-PAGE, stained with Coomassie blue and analyzed by autoradiography (see FIG. 9). The bacterially expressed IKKB is able to phosphorylate TRIP9 (human IIK beta) but not TRIP9/AA (FIG. 9, lanes 3 and 4). For a brief outline of the experiment see FIG. 13.

EXAMPLE 8

IKK3 Mediates the Expression of Various Chemokines and Cytokines

Figure 10:
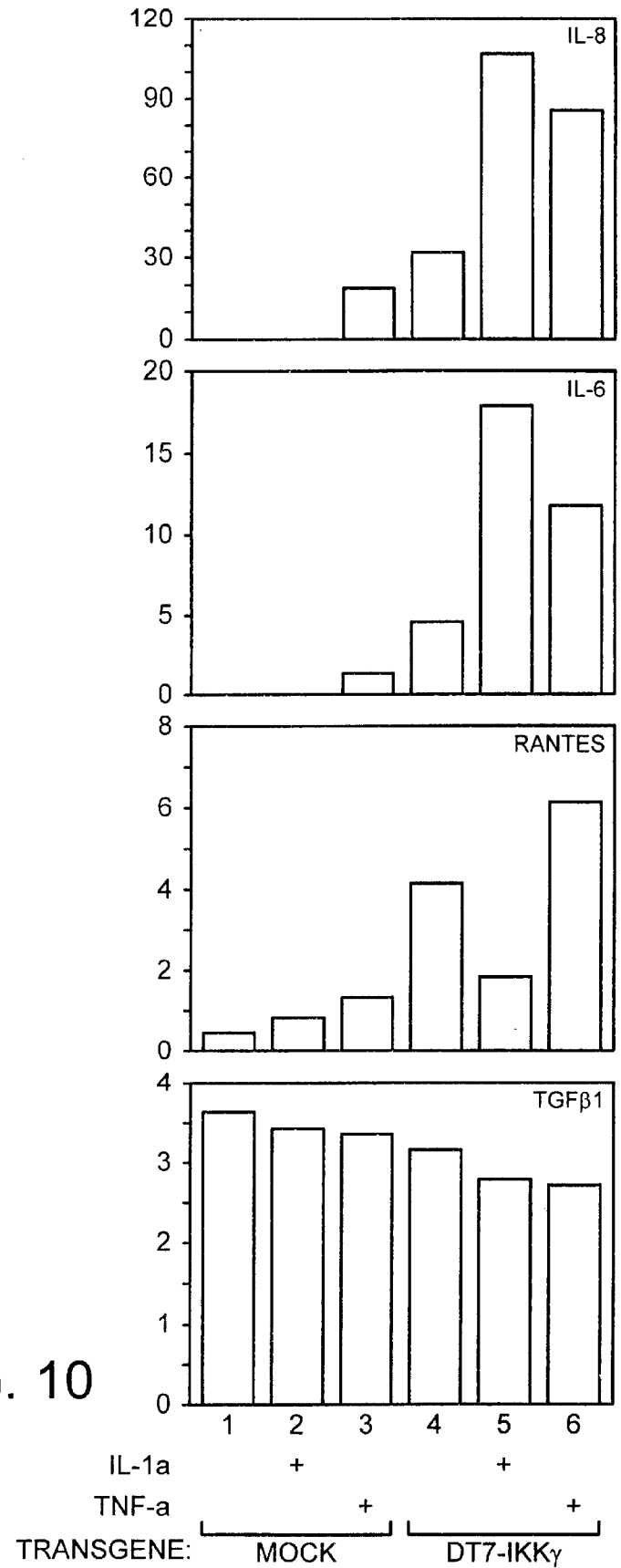

Hela cells were stably expressed with the double T7-tagged IKK3 expression vector (DT7-IKK3) or control vector (Mock). The cells were treated with IL-1α (10 ng/ml) or TNF-α (100 ng/ml) for 5 hours. Total RNAs were purified from these cells and subject to Rnase protection assay. The bands of IL 8, IL-8, RANTES and TGFbeta1 were normalized by the G3PDH expression, respectively (see FIG. 10). It was found that over expression of IKK3 in Hela cells leads to the expression of IL-8, IL-6 and RANTES in Hela cells (see FIG. 10).

EXAMPLE 9

IKK3 Mediates the Expression of IL-8 RNA

Figure 11:
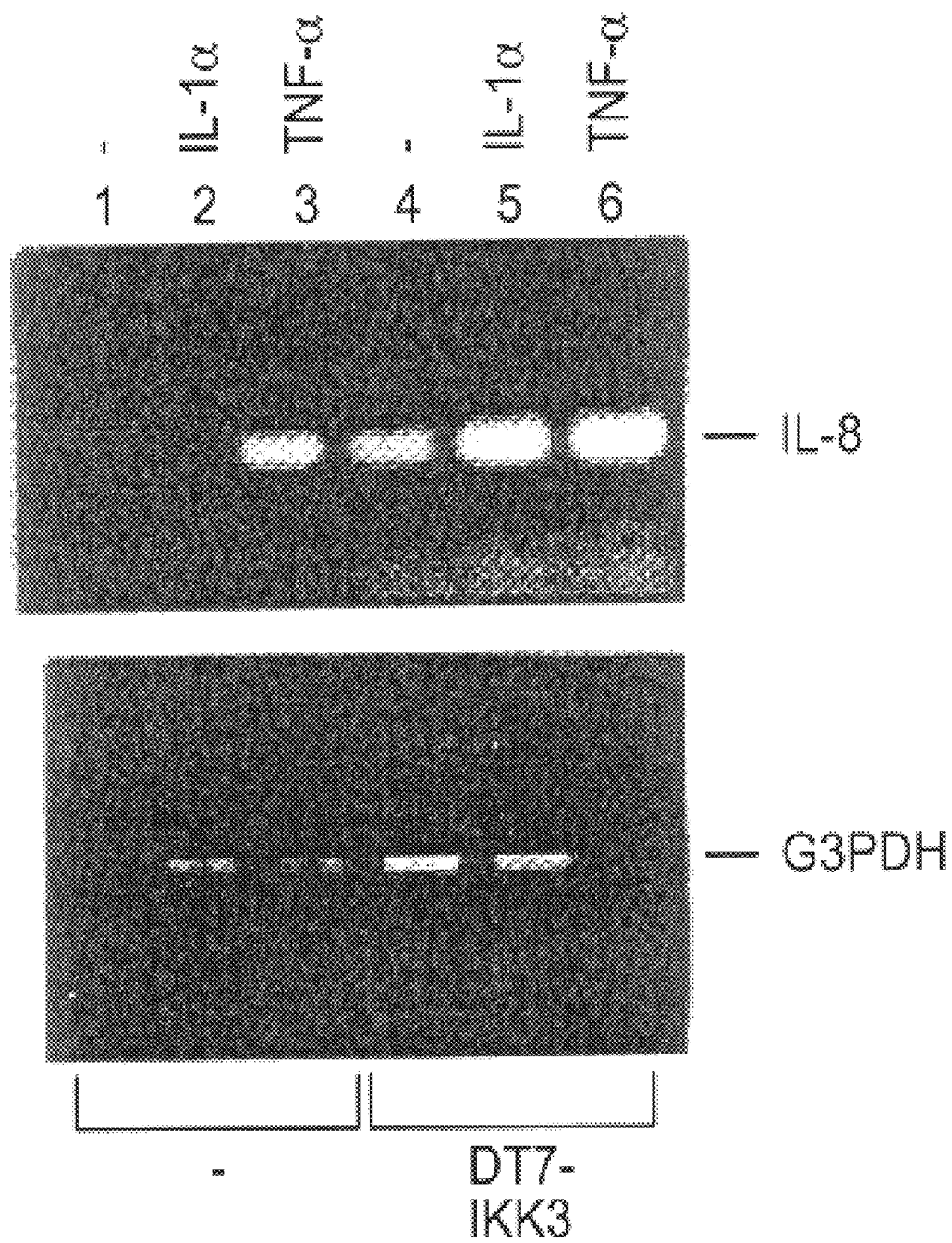

Hela cells were stably expressed with double T7-tagged IKK3 (DT7-IKK3) or Mock (−). The cells were treated with IL-1α (10 ng/ml) or TNF-α (100 ng/ml). Total RNAs were purified from these cells and subjected to RT-PCR analysis with oligonucleotide primers specific for IL-8. PCR amplification of G3PDH was used as an internal control. After 30 cycles, the PCR products were sized-fractionated onto a 1.8% agarose gel and stained with ethidium bromide (see FIG. 11).

EXAMPLE 10

IKK3 Regulates the NF-κB Site of IL-8

The IL-8 promoter contains an NF-kB binding site and the site is a critical element for IL-8 gene regulation. To test whether IKK3 regulates the NF-κB site of IL-8, a reporter gene construct, containing the IL-8 promoter, was constructed. DT7-IKK3 was transiently expressed in Hela cells with the IL-8 reporter genes. The mutant reporter construct contains 4 copies of the NF-kB binding site, of which 3 contained 2 point mutations. IKK3 activates the IL-8 reporter gene, though IKK3 is unable to activate the mutant reporter. These observations indicate that IKK3 is one of several critical kinases that controls the IL-8 gene regulation via the NF-κB site.

Cells and Transfection

Hela cells were maintained in Dulbecco's modified Eagle's medium (DMEM) with 10% fetal calf serum. DNA transfection into cells was performed using DOSPER transfection according to the manufacture's instructions.

Vector Construction

PLuc-neo reporter gene was constructed as follows: pd2EGFP-1 (Clonetech) was digested with BglII-SacII, Klenow-repaired and ligated to remove multi-cloning site. The plasmid was digested with Bsp120-AflII and Klenow-repaired. The DNA fragment containing Neo gene was used for the vector construction. PGL3-basic (Invitrogen) was digested with SalI/NotI, and Klenow-repaired. The DNA fragment containing Luciferease gene was ligated with the DNA containing the Neo gene derived from pd2EGFP-1. The vector was termed as pLuc-neo basic. Two synthetic complementary oligonucleotides of the promoter region of the IL-8 gene containing an NF-kB binding site (from −1 to 196) were annealed and digested with HindIII and KpnI. The resulting cDNA fragment was subcloned into a HindIII/KpnI site of the pLuc-neo. Next, two complementary oligonucleotide, containing 3 repeats of the IL-8 NF-kB site (primers G165/194 and G166/195) were annealed, digested with KpnI and subcloned into a KpnI site of the IL-8 NF-kB reporter gene. Finally, a vector, containing 3 copies of a mutant NF-kB binding site, (2 point mutations), was constructed (primers G167/194 and G168/196).

IKK3 controls an essential step in the NF-kB signalling pathway. Hela cells were transiently transfected with the IL-8 or the IL-8 mutant luciferase reporter gene plasmid, and the expression vector encoding double T7-tagged IKK3 (IKK3), or with a vector control (Mock). Luciferase activities were determined and normalized on the basis of β-galactosidase expression from cotransfected pact-β-Gal. (See FIG. 14).

EXAMPLE 11

Expression of IKK3

In the previous report, we showed that the IKK3 mRNA is inducible with IL-1 and TNF-alfa. To test the expression of the mRNA in human tissues, GENE HUNTER (TOYOBO) was used. The IKK3 expression was detected in the Liver, Pancreas, Placenta and Lung, but not in the Heart and Brain.

Northern Blot Analysis

Cells were treated with IL-1α (10 ng/ml), TNF-α (100 ng/ml), IFN-γ (10 ng/ml), LPS (100 ng/ml) or C2-ceramide (50 $\mu$M) for 5 hours, and the total RNAs were analyzed by Northern blot analysis with the IKK3 specific primers. The expression of actin RNA was used as a control. (See FIG. 15).

EXAMPLE 12

IKK3 Antibody

Figure 1:
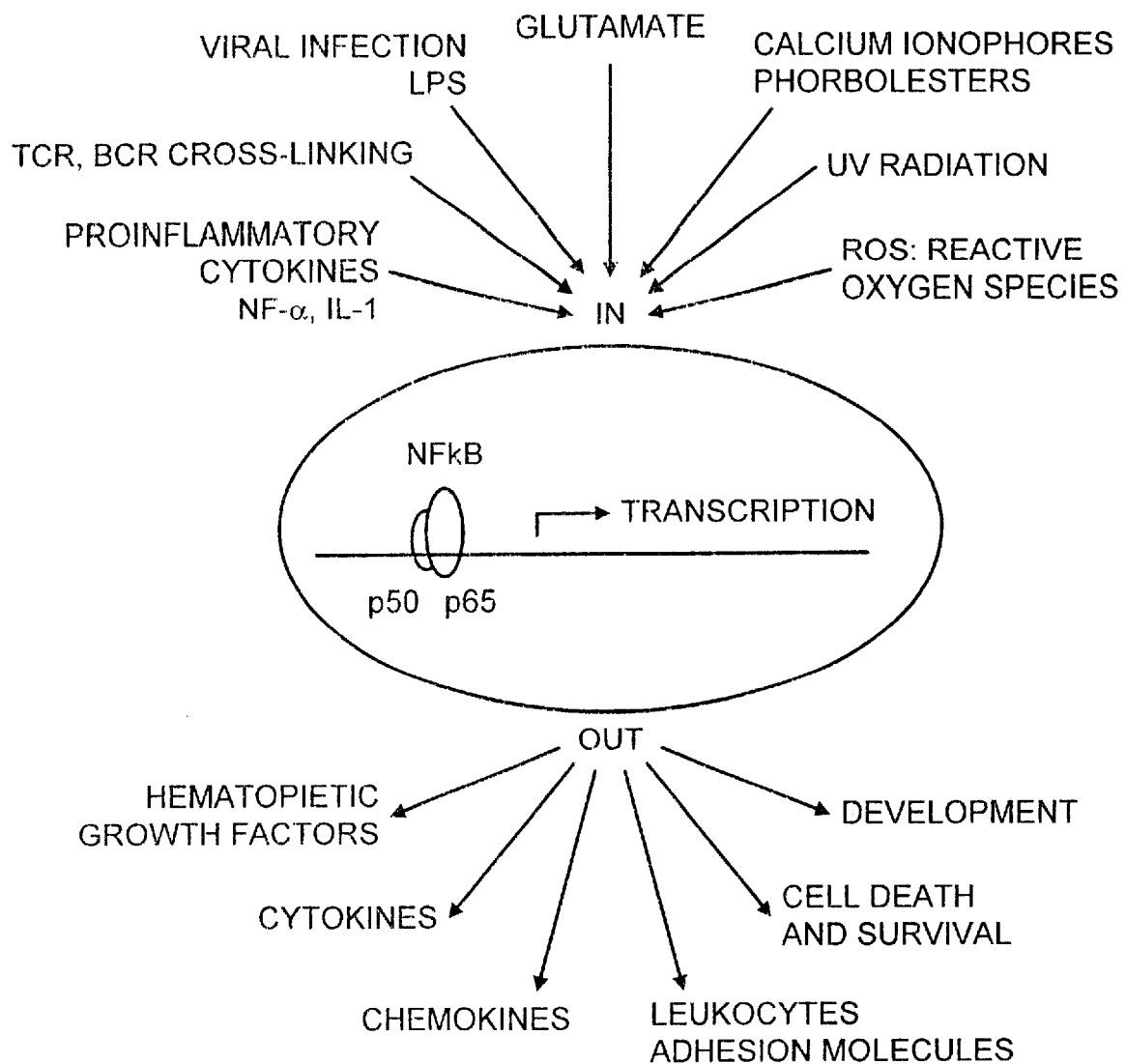
FIG. 1
Figure 2:
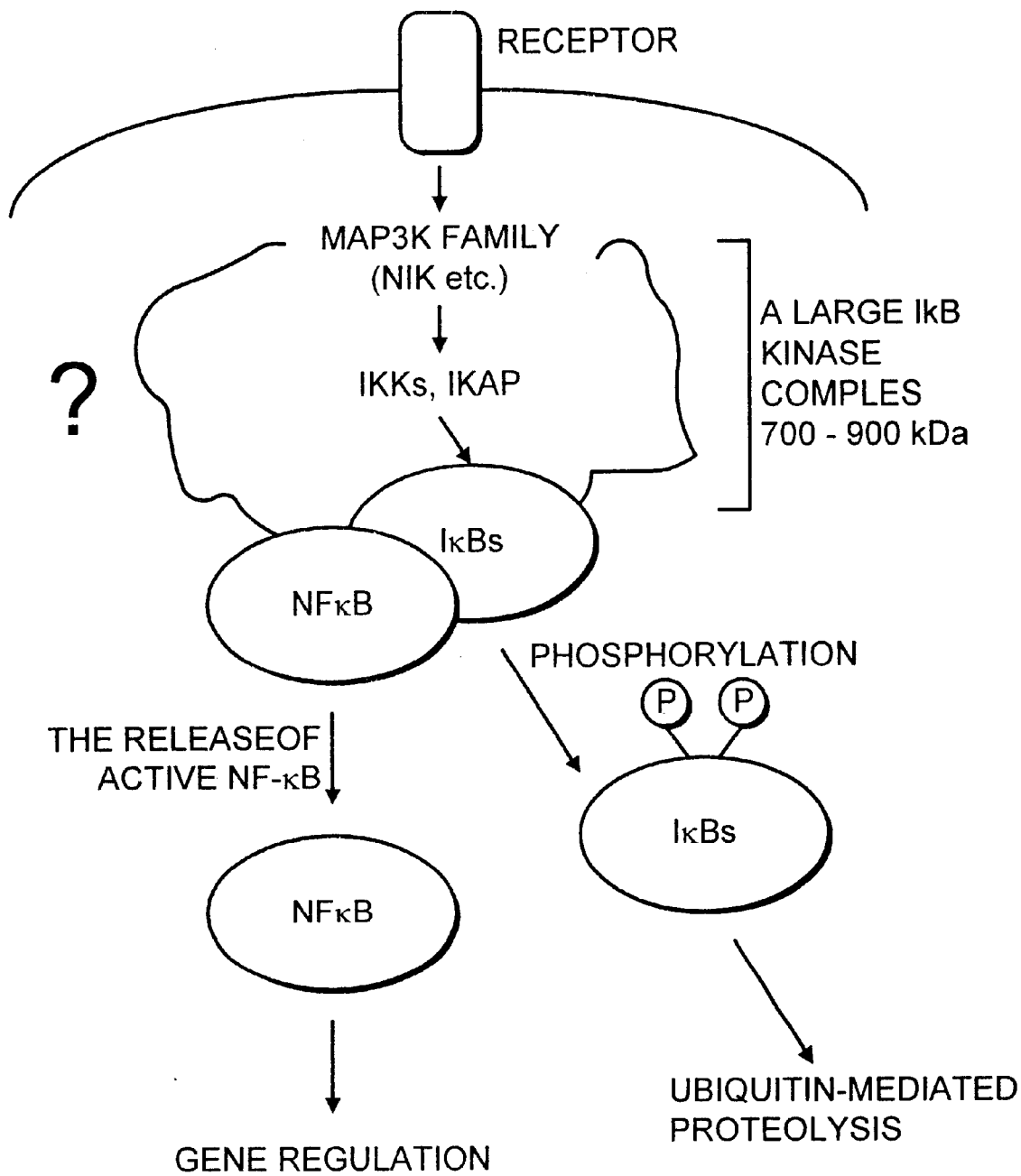

Anti-IKK3 polyclonal antibodies were derived from rabbits immunized the GST-IKK-NT and GST-IKK-CT fusion proteins (FIG. 1A). The antibodies are available for the immunoporecipitation of the IKK3 molecules (data not shown). To test the effect of the antibody against the IKK3 kinase activity, we pre-incubated GST-IKK3 molecule with the antibodies and performed in vitro kinase assay. The antibodies against IKK3 increased the kinase activity (FIG. 1B).

Antibody

Anti-IKK3 antibodies were generated in rabbits immunized with GST, GST-IKK3-NT (amino acids K69-P193) and GST-IKK3-CT (amino acids V628-V716), respectively.

IKK3-NT: nucleotides 531–560 5' primer G99 nucleotides 879–905 3' primer G100

IKK3-CT: nucleotides 2208–2237 5' primer G103 nucleotides 2448–2477 3' primer G86

The PCR fragments were subcloned into a NotI site of pGEX4T-2.

G86: 5'-CCCCCCGCGGCCGCCTCAGACATCAGG-AGGTGCTGGGACTCTATT-3'

G99: 5'-CCCCCCGCGGCCGCCAAGCTCTTTGCG-GTGGAGGAGACGGGCGGA-3'

G100: 5'-CCCCCCGCGGCCGCCTCAGGGCTTTC-GAAGCACCGCCCGCTCATA-3'

G103: 5'-CCCCCCGCGGCCGCCGTGGCTGCCTG-TAACACAGAAGCCCAGGGG-3'

What is claimed is:

1. A method for identification of a compound which exhibits IKK3 kinase modulating activity, comprising contacting a IKK3 kinase protein selected from:
   (a) a protein comprising SEQ ID NO:2; and
   (b) a protein having at least 95% sequence identity to SEQ ID NO:2;
with a test compound and detecting modulating activity.

2. A method of screening a test compound to identify IKK3 modulating activity, comprising contacting:
   (a) a known IKK3 substrate;
   (b) an IKK3 protein selected from:
      (i) a protein comprising SEQ ID NO:2;
      (ii) a protein having at least 95% sequence identity to SEQ ID NO:2 and capable of phosphorylating said known IKK3 substrate; and
   (c) a test compound, under conditions suitable for the phosphorylation of the substrate by IKK3, and detecting whether phosphorylation of the substrate is increased or decreased in the presence of the test compound compared to that which would occur in the absence of the test compound, where an increase or decrease in substrate phosphorylation indicates said test compound has IKK3 modulating activity.

3. A method according to claim 2 where said IKK3 substrate is selected from the group consisting of IkBα, IkBβ, IkBε, and TRIP9.

* * * * *